US005747517A

United States Patent [19]

Panetta et al.

[11] Patent Number: 5,747,517
[45] Date of Patent: May 5, 1998

[54] BENZYLIDENE RHODANINES

[75] Inventors: Jill A. Panetta, Zionsville; Michael L. Phillips, Indianapolis; Jon K. Reel, Carmel; John K. Shadle, Fishers; Sandra K. Sigmund, Indianpolis; Richard L. Simon; Celia A. Whitesitt, both of Greenwood, all of Ind.

[73] Assignee: Eli Lilly and Company, Indianapolis, Ind.

[21] Appl. No.: 710,102

[22] Filed: Sep. 11, 1996

Related U.S. Application Data

[62] Division of Ser. No. 213,873, Mar. 16, 1994.

[51] Int. Cl.$^6$ .................. C07D 277/34; A61K 31/425
[52] U.S. Cl. ............................ 514/369; 548/183
[58] Field of Search .................. 548/183; 514/369

[56] References Cited

U.S. PATENT DOCUMENTS

| | | | |
|---|---|---|---|
| 4,287,200 | 9/1981 | Kawamatsu et al. | 514/369 |
| 4,376,777 | 3/1983 | Kawamatsu et al. | 514/369 |
| 4,387,101 | 6/1983 | Kawamatsu et al. | 514/369 |
| 4,461,902 | 7/1984 | Kawamatsu et al. | 514/369 |
| 4,552,891 | 11/1985 | Ho et al. | 514/369 |
| 4,617,312 | 10/1986 | Schnur | 514/369 |
| 4,636,516 | 1/1987 | Kubo et al. | 514/369 |
| 4,703,052 | 10/1987 | Eggler et al. | 514/369 |
| 4,714,765 | 12/1987 | Ogawa | 514/369 |
| 4,863,923 | 9/1989 | Ho et al. | 514/369 |
| 4,948,900 | 8/1990 | Iijima et al. | 514/369 |
| 4,997,948 | 3/1991 | Zask et al. | 514/369 |
| 5,158,966 | 10/1992 | Lafferty et al. | 514/369 |
| 5,208,250 | 5/1993 | Ceterko | 514/364 |
| 5,523,314 | 6/1996 | Rue-Valleskey | 514/364 |

FOREIGN PATENT DOCUMENTS

| | | |
|---|---|---|
| 0045165 A1 | 2/1982 | European Pat. Off. |
| 0208420 | 6/1986 | European Pat. Off. |
| 0193256 A1 | 9/1986 | European Pat. Off. |
| 0211670 A2 | 2/1987 | European Pat. Off. |
| 0212617 A1 | 3/1987 | European Pat. Off. |
| 0343643 A2 | 11/1989 | European Pat. Off. |
| 0391644 A2 | 10/1990 | European Pat. Off. |
| 0398179 A1 | 11/1990 | European Pat. Off. |
| 0449216 al | 2/1991 | European Pat. Off. |
| 0434394 A2 | 6/1991 | European Pat. Off. |
| 0047109 A1 | 3/1992 | European Pat. Off. |
| 0500337 A1 | 8/1992 | European Pat. Off. |
| 0569777 A2 | 11/1993 | European Pat. Off. |
| 0237133 A1 | 9/1997 | European Pat. Off. |
| 1038050 | 9/1958 | Germany. |
| 40 27 038 A1 | 3/1992 | Germany. |
| 226617 | 9/1968 | U.S.S.R. |
| 2249788 | 5/1992 | United Kingdom. |

OTHER PUBLICATIONS

H.J. Teuber, et al., *Liebigs Ann. Chem*, 757 (1978).
Katsumi, et al., *Chem. Pharm. Bull*, 34:1619 (1986).
Chakrabati, et al., *Tetrahedron* 2781 (1969).
Roggero, et al., *Bull. De La Societe Chimique De France*, 11:4021 (1971).
Patent Abstracts of Japan, 11(232) (C–437) [2679] 1987, *abstracting*, JP 62–45553.
Allan, et al., *Journal of Organic Chemistry*, 23:112 (1958).
Fujita, et al., *Diabetes*, 32:804 (1983).
Sohda, et al., *Chem. Pharm. Bull.*, 30:3563 (1982).
Sohda, et al., *Chem. Pharm. Bull.*, 30:3580 (1982).
Sohda, et al., *Chem. Pharm. Bull.*, 32:2267 (1984).
Tomisawa, et al., *Chem. Pharm. Bull.*, 34:701 (1986).
Isomura, et al., *Chem. Pharm. Bull.*, 32:152 (1984).
Patent Abstracts of Japan, 11(232) (C–433) [2653] 1987, *abstracting*, JP 62–29570.
Derwent Abstracts, 87–076383/11, abstracting, J6 2029–579A no date.

*Primary Examiner*—Robert Gerstl
*Attorney, Agent, or Firm*—Paul J. Gaylo; David E. Boone

[57] ABSTRACT

This invention provides novel benzylidene rhodanines which are useful as agents in treating or preventing conditions associated with β-amyloid peptide. This invention further provides methods of treating or preventing Alzheimer's Disease which comprises administering to a mammal in need thereof an effective amount of one or more of the benzylidene rhodanines of the present invention.

16 Claims, No Drawings

BENZYLIDENE RHODANINES

BACKGROUND OF THE INVENTION

This application is a division of application Ser. No. 08/213.873 filed Mar. 16, 1994.

Alzheimer's disease is a degenerative disorder of the human brain. Clinically, it appears as a progressive dementia. Its histopathology is characterized by degeneration of neurons, gliosis, and the abnormal deposition of proteins in the brain. Proteinaceous deposits (called "amyloid") appear as neurofibrillary tangles, amyloid plaque cores, and amyloid of the congophilic angiopathy. [For reviews, see, *Alzheimer's Disease*, (B. Reisberg, ed., The Free Press 1983).]

While there is no general agreement as to the chemical nature of neurofibrillary tangles, the major constituent of both the amyloid plaque cores and the amyloid of the congophilic angiopathy has been shown to be a 4500 Dalton protein originally termed β-protein or amyloid A4. Throughout this document this protein is referred to as β-amyloid peptide or protein.

β-amyloid peptide is proteolytically derived from a transmembrane protein, the amyloid precursor protein. Different splice forms of the amyloid precursor protein are encoded by a widely expressed gene. see, e.g., K. Beyreuther and B. M üller-Hill, *Annual Reviews in Biochemistry*, 58:287–307 (1989). β-amyloid peptide consists, in its longest forms, of 42 or 43 amino acid residues. J. Kang, et al., *Nature (London)*, 325:733–736 (1987). These peptides, however, vary as to their amino-termini. C. Hilbich, et al., *Journal of Molecular Biology*, 218:149–163 (1991).

Because senile plaques are invariably surrounded by dystrophic neurites, it was proposed early that β-amyloid peptide is involved in the loss of neuronal cells that occurs in Alzheimer's disease. B. Yankner and co-workers were the first to demonstrate that synthetic β-amyloid peptide could be neurotoxic in vitro and in vivo. B. A. Yankner, et al., *Science*, 245:417 (1989); See, also, N. W. Kowall, et al., *Proceedings of the National Academy of Sciences, U.S.A.*, 88:7247 (1991). Other research groups, however, were unable to consistently demonstrate direct toxicity with β-amyloid peptide. See, e.g., *Neurobiology of Aging*, 13:535 (K. Kosik and P. Coleman, eds. 1992). Even groups receiving β-amyloid peptide from a common source demonstrate conflicting results. D. Price, et al., *Neurobiology of Aging*, 13:623–625 (1991)(and the references cited therein).

As mentioned supra, cells have alternative mechanisms for processing amyloid precursor protein which can result in the formation of the β-amyloid protein and subsequently, the senile plaques. It is likely that this alternative processing route occurs in the lysosomes. It has been found that compounds that inhibit lysosomal enzymes inhibit the fragment formation. See, e.g., *Science*, 255:689 (1992).

A lysosome is a membranous reservoir of hydrolytic enzymes responsible for the intracellular digestion of macromolecules. Lysosomes are known to contain approximately forty hydrolytic enzymes, including proteases, nucleases, glycosidases, lipases, phospholipases, phosphatases and sulfatases. These enzymes are all acid hydrolases which are optimally active at about pH 5. Therefore, it is necessary to determine which enzyme or enzymes are responsible for this alternative processing of the amyloid precursor protein and the consequent formation of the β-amyloid protein.

Abnormally high concentrations of the proteases cathepsins D and B have been observed in the brains of patients with early-onset Alzheimer's disease. Yu Nakamura, et al, *Neuroscience Letters*, 130, 195–198 (1991). The cathepsins are a family of hydrolase enzymes that are usually located in the lysosomes. These enzymes are endopeptidases with an acidic optimum pH. Cathepsin A is a serine carboxypeptidase, cathepsin C [EC 3.4.14.1] is a dipeptidyl peptidase, cathepsin D [EC 3.4.23.5] is an aspartyl protease, and cathepsin $B_2$ [EC 3.4.16.1] is a serine carboxypeptidase. Cathepsin B [EC 3.4.22.1] (also known as cathepsin $B_1$) and cathepsin L [EC 3.4.22.15] are thiol proteases having activity within the lysosomes.

Abnormally high concentrations of the proteases cathepsins D and B have been observed in the brains of patients with early-onset Alzheimer's disease. Yu Nakamura, et al., *Neuroscience Letters*, 130:195–198 (1991). Furthermore, elevated activity for cathepsin D has been observed in the brains of Alzheimer's patients. M. Takeda, et al., *Neurochemistry Research*, (abstract), 11:117 (1986). Cathepsin D is a lysosomal endoprotease that is present in all mammalian cells. See, e.g., "Proteinases in Mammalian Cells and Tissues," ed. (A. J. Barret, ed. 1977) pp. 209–248. It is the only aspartyl protease that is known to be a lysosomal enzyme.

It has been found that inhibition of cathepsin D using an aspartyl protease inhibitor reduces the formation of β-amyloid protein and the resultant senile plaque. These and other aspects of the present invention are discussed in greater detail below.

Because of the debilitating effects of Alzheimer's disease there continues to exist a need for effective treatments. This invention provides methods for the treatment of Alzheimer's disease in mammals. Specifically, this invention provides methods of using inhibitors which are specific for the subgroup of cathepsins which are aspartyl proteases as a treatment for Alzheimer's disease.

SUMMARY OF THE INVENTION

This invention provides a method for treating or preventing Alzheimer's disease in a mammal which comprises administering to a mammal in need thereof an effective amount of a compound of Formula I

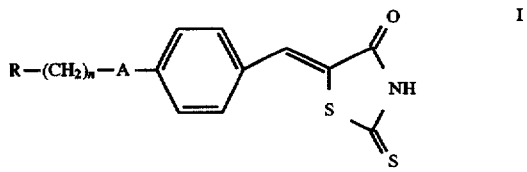

wherein:

n is 0, 1, 2, 3, or 4;

A is oxygen or sulfur;

R is phenyl or naphthyl optionally substituted with one or more substituents selected from the group consisting of $C_1$–$C_{10}$ alkyl, $C_2$–$C_{10}$ alkanoyl, $C_1$–$C_{10}$ haloalkyl, hydroxy, hydrogen, phenyl, phenyl($C_1$–$C_6$ alkylidenyl)-, heterocycle, heterocycle($C_1$–$C_6$ alkylidenyl)-, unsaturated heterocycle, unsaturated heterocycle($C_1$–$C_6$ alkylidenyl)-, halo, $C_1$–$C_{10}$ alkylamino, $C_1$–$C_{10}$ alkoxy, benzoyl, and $C_1$–$C_{10}$ alkylthio, said phenyl, phenyl($C_1$–$C_6$ alkylidenyl)-, benzoyl, heterocycle, heterocycle($C_1$–$C_6$ alkylidenyl)-, unsaturated heterocycle($C_1$–$C_6$ alkylidenyl)-, and unsaturated heterocycle moieties being optionally substituted with one or more halo, $C_1$–$C_6$ alkyl, or $C_1$–$C_6$ alkoxy groups;

or a pharmaceutically acceptable salt thereof.

In another embodiment this invention provides the novel compounds of Formula I and the pharmaceutically acceptable salts thereof as well as formulations comprising a compound of Formula I in combination with one or more pharmaceutically acceptable carriers, excipients or diluents.

DETAILED DESCRIPTION AND PREFERRED EMBODIMENTS

The terms and abbreviations used in the instant examples have their normal meanings unless otherwise designated. For example "C" refers to degrees Celsius; "N" refers to normal or normality; "mmol" refers to millimole or millimoles; "g" refers to gram or grams; "ml" means milliliter or milliliters; "M" refers to molar or molarity; "FDMS" refers to field desorption mass spectrometry; "IR" refers to infrared spectroscopy; and "NMR" refers to nuclear magnetic resonance spectroscopy. All units of measurement employed herein are in weight units except for liquids which are in volume units.

As used herein, the term "$C_1$–$C_{10}$ alkyl" refers to straight or branched, monovalent, saturated aliphatic chains of 1 to 10 carbon atoms and includes, but is not limited to, methyl, ethyl, propyl, isopropyl, butyl, isobutyl, t-butyl, pentyl, isopentyl, and hexyl. The term "$C_1$–$C_{10}$ alkyl" includes within its definition the term "$C_1$–$C_6$ alkyl".

"$C_1$–$C_{10}$ alkylidenyl" refers to a straight or branched, divalent, saturated aliphatic chains of 1 to 10 carbon atoms and includes, but is not limited to, methylenyl, ethylenyl, propylenyl, isopropylenyl, butylenyl, isobutylenyl, t-butylenyl, pentylenyl, isopentylenyl, hexylenyl, octylenyl, decylenyl. The term "$C_1$–$C_6$ alkylidenyl" is encompassed within the term "$C_1$–$C_{10}$ alkylidenyl".

"Halo" represents chloro, fluoro, bromo or iodo. "$C_1$–$C_6$ alkylthio" represents a straight or branched alkyl chain having from one to four carbon atoms attached to a sulfur atom. Typical $C_1$–$C_6$ alkylthio groups include methylthio, ethylthio, propylthio, isopropylthio, butylthio and the like. The term "$C_1$–$C_6$ alkylthio" includes within its definition the term "$C_1$–$C_4$ alkylthio".

"$C_2$–$C_{10}$ alkanoyl" represents a straight or branched alkyl chain having from one to ten carbon atoms attached to a carbonyl moiety. Typical $C_2$–$C_{10}$ alkanoyl groups include ethanoyl, propanoyl, isopropanoyl, butanoyl, t-butanoyl, pentanoyl, hexanoyl, 3-methylpentanoyl and the like.

"$C_1$–$C_4$ alkylamino" represents a group of the formula

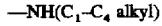
—NH($C_1$–$C_4$ alkyl)

wherein a chain having from one to four carbon atoms is attached to an amino group. Typical $C_1$–$C_4$ alkylamino groups include methylamino, ethylamino, propylamino, isopropylamino, butylamino, sec-butylamino and the like.

"Di($C_1$–$C_4$ alkyl)amino" represents a group of the formula

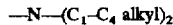
—N—($C_1$–$C_4$ alkyl)$_2$ wherein two alkyl chains, each independently having from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

The term "$C_1$–$C_{10}$ haloalkyl" as used herein refers to a straight or branched $C_1$–$C_{10}$ alkyl chain having at least one halo group attached to it. Typical $C_1$–$C_{10}$ haloalkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, 3-chloro-7-iodooctyl, and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_3$–$C_8$ cycloalkyl" represents a saturated hydrocarbon ring structure containing from three to eight carbon atoms. Typical $C_3$–$C_8$ cycloalkyl groups include cyclobutyl, cyclohexyl, cyclopentyl, cyclohexyl, cycloheptyl and the like.

As noted supra, this invention includes the pharmaceutically acceptable salts of the compounds defined by Formula I. A compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, 7-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

As would be understood by the skilled artisan, throughout the synthesis of the compounds of Formula I it may be necessary to employ an amino-protecting group, a hydroxy-protecting group, or a carboxy-protecting group in order to reversibly preserve a reactively susceptible amino, hydroxy, or carboxy functionality while reacting other functional groups on the compound.

Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is not critical so long as the derivatized amino group is stable to the condition of subsequent reactions) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of these groups are found in E. Haslam, "Protective Groups in Organic Chemistry", (J. G. W. McOmie, ed., 1973), at Chapter 2; and T. W Greene and P. G. M. Wuts, "Protective Groups in Organic Synthesis" (1991), at Chapter 7.

Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxy-benzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5; and T. W. Greene and P. G. M. Wuts, supra, at Chapter 5.

Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, $C_1$–$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl. Further examples of these groups are found in T. W. Greene and P. G. M. Wuts, supra at Chapter 3.

The preferred compounds of the present invention as well as the compounds preferred in the methods of the present invention are those compounds of Formula I wherein:

1) A is oxygen;
2) R is substituted phenyl; and
3) n is 0–3.

The more preferred compounds of the present invention as the compounds preferred in the methods of the present invention are those compounds of Formula I wherein:

1) A is oxygen;
2) n is 1 or 2; and
3) R is phenyl which is substituted at the 2-position and is optionally substituted elsewhere.

The most preferred compounds of the present invention are those wherein R is phenyl substituted at the 2-position with $C_1$–$C_6$ alkyl, $C_1$–$C_6$ alkoxy, halo, or $C_1$–$C_6$ alkylthio.

The compounds of the present invention, as well as the compounds employed in the methods of the present invention, can typically be prepared by methods well known to one skilled in the art of organic chemistry. For example, such compounds may be prepared by condensation of rhodanine, or an appropriately protected rhodanine derivative, with an appropriately substituted aromatic aldehyde or an aldehyde derivative such as a mono or disubstituted imine of the formulae

This type of reaction is illustrated utilizing an appropriately substituted aromatic aldehyde as follows

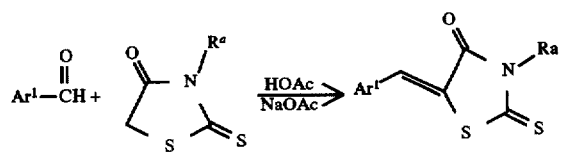

wherein $R^a$ is hydrogen or an amino-protecting group and $Ar^1$ is equal to

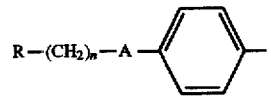

or an appropriately protected derivative thereof.

It will be readily appreciated by one skilled in the art that the aryl portion of the present compounds of Formula I are either commercially available or may be readily prepared by known techniques from commercially available starting materials. For example, 4-hydroxybenzaldehyde, or a substituted derivative thereof, may be alkylated under Friedel-Crafts conditions to yield an alkylbenzaldehyde which in turn may itself be alkylated. Similarly, the rhodanine or N-substituted rhodanine starting material is either commercially available or may be prepared by well known methodology from commercially available starting materials as demonstrated in the examples infra.

It will be readily appreciated by one skilled in the art that the aromatic portion of the compounds of the invention (or the compounds employed in the methods of the present invention) can be provided by compounds which are either commercially available or may be readily prepared by known techniques from commercially available starting materials. Similarly, the rhodanine or N-substituted rhodanine starting material is either commercially available or may be prepared by well known methods from commercially available substrates.

The following examples further illustrate the preparation of compounds which may be employed in the method of treating or preventing Alzheimer's Disease provided by this invention. The examples are illustrative only and are not intended to limit the scope of the invention in any way. The terms "NMR", "IR" or "FDMS", "MS" following a synthesis protocol indicates that the nuclear magnetic resonance spectrum, infrared spectrum, field desorption mass spectrometry, or the mass spectrometry was performed and was consistent with the title product.

EXAMPLE 1
Preparation of 5-[[4-[(4-acetyl-3-hydroxy-2-propylphenyl)methoxy]phenyl]methylene]-2-thioxo-4-thiazolidinone 3-Methoxybenzaldehyde (408 g, 3.00 moles) was dissolved in ethanol and then hydrogenated by catalytic hydrogenation in the presence of 5% palladium on activated carbon (20 g) in the presence of dimethylamine (678 g of a 40% aqueous solution, 6.0 moles). The reaction was allowed to proceed overnight at room temperature.

The solvents were then removed in vacuo and the residue was dissolved in diethyl ether. This solution was thrice washed with water and dried over sodium sulfate. The solvents were removed in vacuo. The residue was further purified by distillation (bp 90°–94° C.) to yield 444.9 grams (89.7%) of the intermediate 1-(N,N-dimethylamino)methyl-3-methoxybenzene.

In two liters of tetrahydrofuran was dissolved 1-(N,N-dimethylamino)methyl-3-methoxybenzene (330 g, 2.0 moles) prepared supra. To this solution was added n-butyl lithium (2.2 moles). The resulting solution was then cooled to 0C and stirred for about four hours. 1-Iodopropane (374 g, 2.2 moles) was then added slowly while stirring. After the addition was completed the reaction mixture was stirred for about one hour at 0C, followed by stirring for about 24 hours at room temperature. To this reaction mixture was then added 200 ml of water. The organic fraction was removed, washed with water, and dried over sodium sulfate. The solvents were removed in vacuo.

The residue was then picked up in diethyl ether and washed thrice with water and then dried over sodium sulfate. The solvents were removed in vacuo and the residue was further purified by distillation (bp 75°–80° C.) to yield 289.1 grams (69.8%) of 1-(N,N-dimethylamino)methyl-3-methoxy-2-propylbenzene.

The 1-(N,N-dimethylamino)methyl-3-methoxy-2-propylbenzene was then converted to the 3-hydroxy equivalent by adding the 1-(N,N-dimethylamino)methyl-3-methoxy-2-propylbenzene (238 g, 1.15 moles) to acetic acid (2.35 L) and then adding hydrobromic acid (1 L of a 48% solution). This mixture was then stirred at reflux for thirty hours. The acetic acid was removed and the residue was redissolved in ethanol. The ethanol was then removed and the residue was again redissolved in ethanol. Diethyl ether was added under a precipitate formed. Precipition was allowed to proceed overnight and the precipitate was collected by filtration to yield 216.2 grams (78.9%) of 1-(N,N-dimethylamino)methyl-3-hydroxy-2-propylbenzene hydrobromic salt.

1-(N,N-Dimethylamino)methyl-3-hydroxy-2-propylbenzene hydrobromic salt (216 g, 0.79 mole) was added to 2 liters of methylene chloride. To this mixture was added pyridine (190.2 g, 2.37 moles) and 4-dimethylaminopyridine. To this mixture acetyl chloride (112.3 ml, 123.8 g, 1.58 moles) was added dropwise while cooling in an ice bath. The reaction mixture was stirred for about six hours and then an excess of potassium carbonate was added. The organic fraction was separated, washed with water, and dried over sodium sulfate. The solvents were removed in vacuo and the residue was distilled (bp 90°–95° C.). The distillate was dissolved in 2 liters of an acetone/ether (50:50) mixture. Dry hydrogen chloride was bubbled through the solution until the solution was acidic. The 1-(N,N-dimethylamino)methyl-3-acetoxy-2-propylbenzene hydrochloric salt then precipitated and was recovered by filtration (178.5 g, 83.2%).

The 1-(N,N-dimethylamino)methyl-3-acetoxy-2-propylbenzene hydrochloric salt (190 g, 0.71 mole) was added to a 2 liter flask and heated to 165° C. To this aluminum chloride (188.9 g, 1.42 moles) was added in portions. This mixture was heated for about three hours and then allowed to cool. Water (1 L) was then added and the resulting mixture was basified by the addition of a 1:1 mixture of sodium hydroxide (50%) and ice. This mixture was extracted twice with ethyl acetate. The organic fractions were combined and then washed with water and dried over sodium sulfate. The solvents were removed in vacuo and the residue was further purified by distillation (bp 101° C.) to yield 143.3 grams (85.9%) of 4-acetyl-1-(N,N-dimethylamino)methyl-3-hydroxy-2-propylbenzene.

The 4-acetyl-1-(N,N-dimethylamino)methyl-3-hydroxy-2-propylbenzene (120 g, 0.51 mole) was then dissolved in toluene (600 ml). This solution was then cooled in an ice bath while stirring. Ethyl chloroformate (146 ml, 162.75 g, 1.5 moles) was then added slowly and then the reaction mixture was stirred for one hour while cooling, followed by stirring overnight at room temperature.

Water (400 ml) was then added to the reaction mixutre and the fractions were separated. The organic phase was collected, washed with water, and dried over sodium sulfate. Solvents were removed in vacuo. After high performance liquid chromatography, 96.2 grams (83.6%) of the deisred intermediate, 4-acetyl-3-hydroxy-2-propylbenzyl chloride, was recovered.

Under an argon atmosphere, sodium (2.3 g, 80 mmol) was dissolved in ethanol. To this solution 4-hydroxybenzaldehyde (13.4 g, 110 mmol) was added, followed by the addition of 4-acetyl-3-hydroxy-2-propylbenzyl chloride (15.8 g, 70 mmol) and sodium iodide (11.9 g, 80 mmol). This mixture was filtered and the precipitate was redissolved in a 1:1 mixture of ethyl acetate and water. The layers were separated and the organic fraction was washed thrice with water and then dried over sodium sulfate. The solvents were removed in vacuo. Further purification of 4-(4-acetyl-3-hydroxy-2-propylbenzyloxy)benzaldehyde was achieved by use of high performance liquid chromatography to yield 11.1 grams (50.8%) of this intermediate.

Under a nitrogen atmosphere in a three-neck round bottom flask 4-[(4-acetyl-3-hydroxy-2-propylphenoxy)methyl]benzaldehyde (5.0 g, 16.0 mmol), rhodanine (2.13 g, 16.0 mmol), sodium acetate (4.6 g, 16.0 mmol) and acetic acid (50 ml) were combined and then heated to reflux. The reaction mixture was allowed to reflux. The progress of the reaction was monitored by thin layer chromatography.

After refluxing overnight, the reaction mixutre was poured into 250 ml of ice water and then filtered. The title product (4.3 g, 63.2%)was recrystallized from toluene:ethyl acetate (4:1). mp 217°–218° C.

EXAMPLE 2

Preparation of 5-[[4-(3-phenylpropoxy)phenyl]methylene]-2-thioxo-4-thiazolidinone Under nitrogen purge in a three-neck round bottom flask 4-(3-phenylpropoxy)benzaldehyde (0.79 g, 3.29 mmol) was dissolved in acetic acid (16 ml). To this solution was added sodium acetate (0.94 g, 11.5 mmol) and rhodanine (0.44 g, 3.30 mmol). The reaction mixture was then heated to 100° C. and maintained at this temperature for about three days. The progress of the reaction was monitored by thin layer chromatography (4:1 hexane:ethyl acetate).

The reaction products were removed by filtration and washed lightly with acetic acid, followed by trituration with ethyl ether and filtration. The precipitate was triturated with water and filtered, followed by a wash with ethyl ether. The solvents were removed in vacuo to yield 0.74 grams (63.5 %) of the title product. mp 197°–199° C., NMR, MS.

Analysis for $C_{19}H_{17}NO_2S_2$: Theory: C, 64.20; H, 4.82; N, 3.94. Found: C, 64.03; H, 4.82; N, 3.83.

EXAMPLE 3

Preparation of 5-[[4-(benzyloxy)phenyl]methylene]-2-thioxo-4-thiazolidinone

In a three-neck round bottom flask equipped with a stir bar, condenser, and nitrogen inlets under nitrogen atmosphere 4-benzyloxybenzaldehyde (6.37 g, 30 mmole) was dissolved in acetic acid (150 ml). To this solution sodium acetate (8.61 g, 3.5 eq) was added followed by the slow addition of rhodanine (4.00 g, 30 mmole). The progress of the reaction was monitored by thin layer chromatography (4:1 hexane:ethyl acetate).

After 20 minutes of stirring this reaction mixture at room temperature the temperature of the mixture was raised to 100° C. and maintained at this temperature for about 48 hours. After this period the reaction mixture was cooled to 75° C. and then filtered, the precipitate being washed mildly with acetic acid. The precipitate was triturated with 100 ml of ethyl ether and filtered, followed by trituration with water and filtration. The precipitate was then washed with ethyl ether and the solvents were removed in vacuo to yield 6.95 grams (71%) fo the title product. mp >225° C. NMR, MS.

Analysis for $C_{17}H_{13}NO_2S_2$: Theory: C, 62.36; H, 4.00; N, 4.28. Found: C, 62.60; H, 3.97; N, 4.29.

EXAMPLE 4

Preparation of (Z)-5-[[4-[(4-acetyl-3-hydroxy-2-propylphenoxymethyl)]phenyl]methylene]-2-thioxo-4-thiazolidinone Under a nitrogen atmosphere a three-neck round bottom flask was charged with methyl (4-bromomethyl)benzoate (10.0 g, 43.6 mmol) dissolved in 100 ml of toluene. The colorless solution was cooled to −70° C. After cooling, diisobutylaluminum hydride (100 mmol dissolved in 100 ml of toluene) was added dropwise at a rate such that the internal temperature of the reaction mixture never exceeded −65° C., resulting in the production of an orange-yellow color, followed by clarification of the solution. The progress of the reaction was monitored by thin layer chromatography.

The reaction was quenched by the addition of methanol and was then poured into a solution of potassium sodium tartrate tetrahydrate (Rochelle's salt). The solution was diluted with diethyl ether and stirred vigorously for about thirty minutes. After separation the organic phase was washed with brine, dried over magnesium sulfate, and concentrated in vacuo to yield 9.0 g of 4-bromomethylbenzyl alcohol as a white crystalline solid.

The 4-bromomethylbenzyl alcohol (9.0 g, 43 mmol) was reduced to the corresponding aldehyde by dissolving the above-synthesized intermediate in methylene chloride and then adding pyridinium chlorochromate (14.1 g, 6.5 mmol). The reaction mixture was then allowed to stir at room temperature under a nitrogen atmosphere for about oone hour. The progress of the reaction was monitored by thin layer chromatography. The reaction mixture was then filtered through a CELITE® pad, concentrated in vacuo, and then partitioned between equal volumes of diethyl ether and water. The organic fraction was washed with water, then with brine, and dried over magnesium sulfate. The solvents were removed in vacuo to yield a white crystalline solid. Recrystallization from hot diethyl ether yielded 4.9 grams of 4-(bromomethyl)benzaldehyde as needle-like crystals.

The 4-(bromomethyl)benzaldehyde was condensed with 1-(2,4-dihydroxy-3-propylphenyl)ethanone by first dissolving the 1-(2,4-dihydroxy-3-propylphenyl)ethanone (0.90 g, 4.63 mmol) in N,N-dimethylformamide (60 ml) under a nitrogen atmosphere. To this solution was then added potassium carbonate (0.64 g, 4.63 mmol), potassium iodide (0.74 g, 4.46 mmol), and the above-prepared aldehyde (0.91 g, 4.57 mmol). This mixture was then warmed to 70° C. and maintained at this temperature for about 30 minutes. The progress of the reaction was monitored by thin layer chromatography.

The reaction mixture was then allowed to cool and was diluted with water. The mixture was then extracted with ethyl acetate (2×200 ml). The organic layers were combined, washed with water and then brine, dried over magnesium sulfate, and then concentrated in vacuo. The desired intermediate product, 4-[(4-acetyl-3-hydroxy-2-propylphenoxy) methyl]benzaldehyde, was then further purified by silica gel chromatography.

Under a nitrogen atmosphere in a three-neck round bottom flask 4-[(4-acetyl-3-hydroxy-2-propylphenoxy)methyl] benzaldehyde (0.9 g, 2.88 mmol), rhodanine (0.42 g, 3.15 mmol), sodium acetate (0.28 g, 3.41 mmol) and acetic acid (25 ml) were combined and then heated to reflux. The reaction mixture was allowed to reflux. The progress of the reaction was monitored by thin layer chromatography.

After refluxing for about 3.5 hours, the yellow solution was allowed to cool to room temperature, resulting in the precipitation of the title product as a yellow crystalline material. mp 236°–238° C. FDMS (M+) 427.

Analysis for $C_{22}H_{21}NO_4S_2$: Theory: C, 61.81; H, 4.95; N, 3.28. Found: C, 61.55; H, 4.93; N, 3.14.

EXAMPLE 5

Preparation of 5-[[4-(2-nitrophenoxy)phenyl]methylene]-2-thioxo-4-thiazolidinone Under nitrogen purge in a three-neck round bottom flask 4-(2-nitrophenoxy)benzaldehyde (0.98 g, 4.03 mmol) was dissolved in acetic acid (20 ml) and stirred at room temperature. To this solution was then added sodium acetate (1.16 g, 14.1 mmol) and rhodanine (0.54 g, 4.05 mmol). The reaction mixture was then raised to 100° C. and maintained at this temperature for about 20 hours. The progress of the reaction was monitored by thin layer chromatography.

After the reaction period at 100° C. the reaction mixture was allowed to cool to 50° C. and then poured into 100 ml of water and stirred for about 15 minutes, during which time a precipitate formed. The precipitate was removed by filtration followed by washing with water and drying under vacuum. The precipitate was triturated with 75 ml of ethyl acetate over a steam bath and allowed to cool to room temperature overnight.

The precipitate was removed by filtration was washed with ethanol, followed by a hexane wash. The solvents were then removed in vacuo. mp 218°–219.5° C. NMR, MS.

Analysis for $C_{16}H_{10}N_2O_4S_2$: Theory: C, 53.62; H, 2.81; N, 7.82. Found: C, 53.89; H, 2.87; N, 7.52.

EXAMPLE 6
Preparation of 5-[[4-[(4-acetyl-3-hydroxy-2-propylphenyl)methoxy]phenyl]methylene]-3-methyl-2-thioxo-4-thiazolidinone Under a nitrogen atmosphere in a three-neck round bottom flask 4-[(4-acetyl-3-hydroxy-2-propylphenyl)methoxy]benzaldehyde (90.0 mg, 0.29 mmol) was dissolved in acetic acid (1.5 ml) with stirring. To this solution was added sodium acetate (82.8 mg, 1.00 mmol) and N-methylrhodanine (42.5 mg, 0.29 mmol). The reaction mixture was then heated to 100° C. and maintained at this temperature for about two hours at which time the reaction mixture was raised to the reflux temperature and allowed to reflux for about 28 hours. The reaction progress was monitored by thin layer chromatography.

After the reaction had sufficiently progressed the reaction mixture was allowed to cool and the precipitate was removed by filtration and washed lightly with acetic acid, followed by an ethyl ether wash. The precipitate was triturated with ethyl ether and filtered followed by trituration with water and filtration. The precipitate was washed with ethyl ether and the solvents were removed in vacuo to yield 60 mg (47%) of the title product. mp 153°–155° C. NMR, FDMS.

Analysis for $C_{23}H_{23}NO_4S_2$: Theory: C, 62.56; H, 5.25; N, 3.17. Found: C, 62.82; H, 5.21; N, 3.22.

EXAMPLE 7
Preparation of 5-[[4-[(4-acetyl-3-methoxy-2-propylphenyl)methoxy]phenyl]methylene]-2-thioxo-4-thiazolidinone Under nitrogen atmosphere in a round bottom flask 4-[(4-acetyl-3-methoxy-2-propylphenyl)methoxy]benzaldehyde (0.33 g, 1.01 mmol) was dissolved in 5 ml of acetic acid with stirring. To this solution was added sodium acetate (0.29 g, 3.53 mmol) followed by the addition of rhodanine (0.13 g, 0.98 mmol). The reaction mixture was heated to reflux. The progress of the reaction was monitored by thin layer chromatography. The reaction was allowed to reflux overnight.

After about 27 hours of refluxing the reaction mixture was allowed to cool to 50° C before filtering. The precipitate was washed lightly with acetic acid. The precipitate was triturated with ethyl ether and filtered, followed by a trituration with water and subsequent filtration. The precipitate was washed with ethyl ether and the solvents were removed in vacuo to give 20 mg (44%) of the title product as a yellow solid. mp 198°–199° C. NMR, FDMS.

Analysis for $C_{23}H_{23}NO_4S_2$: Theory: C, 62.56; H, 5.25; N, 3.17. Found: C, 62.73; H, 5.51; N, 2.92.

EXAMPLE 8
Preparation of 5-[[3-[4-(t-butyl)phenoxy]phenyl]methylene]-3-(2-carboxyethyl)-2-thioxo-4-thiazolidinone Under nitrogen atmosphere in a round bottom flask 4-[4-(t-butyl)phenoxy]benzaldehyde (2.0 g, 7.8 mmol) was dissolved in 40 ml of acetic acid with stirring. To this solution was added sodium acetate (2.56 g, 31.2 mmol) followed by the addition of N-(2-carboxyethyl)rhodanine (1.79 g, 8.7 mmol). The reaction mixture was heated to reflux. The progress of the reaction was monitored by thin layer chromatography. The reaction was allowed to reflux overnight.

After about 27 hours of refluxing the reaction mixture was allowed to cool to 50° C. before filtering. The precipitate was washed lightly with acetic acid. The precipitate was triturated with ethyl ether and filtered, followed by a trituration with water and subsequent filtration. The precipitate was recrystallized from a 1:1 methylene chloride:hexane solution to give 1.85 g (54%) of the title product as a yellow solid. mp 141°–147° C.

Analysis for $C_{23}H_{23}NO_4S_2$: Theory: C, 62.56; H, 5.25; N, 3.17. Found: C, 62.34; H, 5.30; N, 3.15.

EXAMPLE 9
Preparation of 5-[[3-[4-(t-butyl)phenoxy]phenyl]methylene]-3-amino-2-thioxo-4-thiazolidinone. mp 127° C.

Analysis of $C_{20}H_{20}N_2O_2S_2$: Theory: C, 62.47; H, 5.24; N, 7.28. Found: C, 62.69; H, 5.41; N, 7.10.

EXAMPLE 10
Preparation of 5-[[4-[(4-acetyl-3-hydroxy-2-propylphenyl)methoxy]phenyl]methylene]-2-thioxo-4-thiazolidinone disodium salt. FDMS.

Analysis of $C_{22}H_{19}NNa_2O_4S_2$: Theory: C, 56.04; H, 4.06; N, 2.97. Found: C, 53.28; H, 4.21; N, 2.42.

EXAMPLE 11
Preparation of 5-[[4-[(4-acetyl-3-hydroxy-2-propylphenyl)methoxy]phenyl]methylene]-2-thioxo-4-thiazolidinone dilithium salt. FDMS, mp >225° C.

Analysis of $C_{22}H_{19}Li_2NO_4S_2$: Theory: C, 60.14; H, 4.36; N, 3.19. Found: C, 57.53; H, 4.61; N, 2.97.

EXAMPLE 12
Preparation of (Z)-5-[[3-[(4-acetyl-3-hydroxy-2-propylphenoxy)methyl]phenyl]methylene]-2-thioxo-4-thiazolidinone Under a nitrogen atmosphere in a three-neck round bottom flask were combined methyl-m-toluate (25.0 g, 166 mmol), N-bromosuccinimide (33.5 g, 188 mmol), 2,2'-azobisisobutyronitrile (3.0 g, 36.5 mmol), and chloroform (200 ml). The resulting mixture was heated to 70° C. and maintained at this temperature for about one hour. The reaction mixture was then allowed to cool to room temperature and then poured into water and vigorously stirred for about 30 minutes and then extracted with chloroform. The organic fraction was washed with water and then dried over sodium sulfate. The solvents were then removed in vacuo, resulting in the formation of crystals. The desired intermediate, 3-bromomethyltoluate, was further purified by liquid chromatography.

A 500 ml round bottom flask was charged with 3-bromomethyltoluate (11.1 g, 45.3 mmol), dissolved in toluene (150 ml). This solution was cooled to −70° C. and then diisobutylaluminum hydride (100 ml of a 1.0M solution dissolved in toluene, 100 mmol) was added dropwise at a rate such that the internal temperature never exceeded −65° C. The progress of the reaction was monitored by thin layer chromatography.

The reaction was quenched by the addition of methanol and then poured into a solution of potassium sodium tartrate tetrahydrate (Rochelle's salt). The mixture was then extracted with diethyl ether. The organic fraction was then washed with brine and then dried over sodium sulfate. The solvents were removed in vacuo to yield 9.3 grams of 3-(bromomethyl)benzyl alcohol.

The 3-(bromomethyl)benzyl alcohol prepared supra was reduced to from the corresponding aldehyde by first dissolving the alcohol (9.3 g, 45 mmol) in methylene chloride. To this solution was added pyridinium chlorochromate (14.0 g, 65 mmol). The resulting mixture was then stirred under a nitrogen atmosphere for about 1.5 hours.

The reaction mixture was then filtered over a CELITE® pad and the solvents were removed in vacuo. The residue was partitioned between equal amounts of diethyl ether and water. The organic fraction was washed in water and then brine, and then dried over sodium sulfate. The solvents were removed in vacuo.

The desired intermediate, 3-(bromomethyl)benzaldehyde, was further purified by liquid chromatography to yield 7.0 grams as a colorless oil.

The 3-(bromomethyl)benzaldehyde was condensed with 1-(2,4-dihydroxy-3-propylphenyl)ethanone by first dissolving the 1-(2,4-dihydroxy-3-propylphenyl)ethanone (1.05 g, 5.41 mmol) in N,N-dimethylformamide (50 ml) under a nitrogen atmosphere. To this solution was then added potassium carbonate (0.76 g, 5.50 mmol), potassium iodide (0.89 g, 5.36 mmol), and the above-prepared aldehyde (1.54 g, 7.2 mmol). This mixture was then warmed to 70° C. and maintained at this temperature for about 25 minutes. The progress of the reaction was monitored by thin layer chromatography.

The reaction mixture was then allowed to cool and was diluted with water. The mixture was then extracted with ethyl acetate and diethyl ether. The organic layers were combined, washed with water and then brine, dried over sodium sulfate, and then concentrated in vacuo. The desired intermediate product, 3-[(4-acetyl-3-hydroxy-2-propylphenoxy)methyl]benzaldehyde, was then recrystallized from hot diethyl ether as a light tan crystalline solid.

Under a nitrogen atmosphere in a three-neck round bottom flask 3-[(4-acetyl-3-hydroxy-2-propylphenoxy)methyl]benzaldehyde (0.73 g, 2.34 mmol), rhodanine (0.34 g, 2.55 mmol), sodium acetate (0.23 g, 2.80 mmol) and acetic acid (20 ml) were combined and then heated to reflux. The reaction mixture was allowed to reflux. The progress of the reaction was monitored by thin layer chromatography.

After refluxing for about five hours, the yellow solution was allowed to cool to room temperature, resulting in the precipitation of a yellow solid which was collected by filtration and then washed with acetic acid and water. The title product was then recrystallized form hot diethyl ether to yield 0.15 grams. mp 213°–215° C. FDMS (M+) 427.

Analysis for $C_{22}H_{21}NO_4S_2$: Theory: C, 61.81; H, 4.95; N, 3.28. Found: C, 58.39; H, 5.14; N, 2.62.

EXAMPLE 13
Preparation of 5-[[3-[4-(t-butyl)phenoxy]phenyl]methylene]-3-(N,N-dimethylamino)-2-thioxo-4-thiazolidinone. mp 113°–116° C.

Analysis of $C_{22}H_{24}N_2O_2S_2$: Theory: C, 64.05; H, 5.86; N, 6.79. Found: C, 63.89; H, 6.00; N, 6.63.

EXAMPLE 14
Preparation of 5-[[4-(4-acetyl-3-hydroxy-2-propylphenyl)methoxy]phenyl]methylene]-2-thioxo-4-thiazolidinone sodium salt.

Analysis of $C_{22}H_{20}NNaO_4S_2$: Theory: C, 58.78; H, 4.49; N, 3.12. Found: C, 59.00; H, 4.20; N, 3.04.

The following compounds were prepared essentially as described above.

EXAMPLE 15
Preparation of 5-[[4-(4-butylphenoxy)phenyl]methylene]-2-thioxo-4-thiazolidinone

EXAMPLE 16
Preparation of 5-[[4-[(4-acetylphenyl)methoxy]phenyl]methylene]-2-thioxo-4-thiazolidinone

EXAMPLE 17
Preparation of 5-[[4-[(3-methoxy-2-propylphenyl)methoxy]phenyl]methylene]-2-thioxo-4-thiazolidinone

EXAMPLE 18
Preparation of 5-[[3-(4-chlorophenoxy)phenyl]methylene]-2-thioxo-4-thiazolidinone

EXAMPLE 19
Preparation of 5-[[3-[4-(1,1,dimethyleth-1-yl)phenoxy]phenyl]methylene]-2-thioxo-4-thiazolidinone

EXAMPLE 20
Preparation of 5-[[4-[(4-acetyl-3-hydroxy-2-propylphenyl)methoxy]phenyl]methylene]-3-(4-cyanobut-1-yl)-2-thioxo-4-thiazolidinone

EXAMPLE 21
Preparation of 5-[[4-[(4-acetyl-3-acetoxy-2-propylphenyl)methoxy]phenyl]methylene]-2-thioxo-4-thiazolidinone

EXAMPLE 22
Preparation of 5-[[4-[4-(t-butyl)phenoxy]phenyl]methylene]-3-(2-carboxyethyl)-2-thioxo-4-thiazolidinone sodium salt

EXAMPLE 23
Preparation of 5-[[4-(4-acetyl-3-hydroxy-2-ethylphenyl)methoxy]phenyl]methylene]-2-thioxo-4-thiazolidinone

EXAMPLE 24
Preparation of 5-[[4-(2,6-dichlorophenyl)methoxy]phenyl]methylene]-2-thioxo-4-thiazolidinone

EXAMPLE 25
Preparation of 5-[[3-(4-butylphenoxy)phenyl]methylene]-2-thioxo-4-thiazolidinone

EXAMPLE 26
Preparation of 5-[[3-[4-(t-butyl)phenoxy]phenyl]methylene]-3-(2-acetoxyeth-1-yl)-2-thioxo-4-thiazolidinone. NMR.

Analysis of $C_{24}H_{25}NO4S_2$: Theory: C, 63.27; H, 5.53; N, 3.07. Found: C, 62.97; H, 5.53; N, 2.98.

EXAMPLE 27
Preparation of 5-[[4-[(4-acetyl-3-hydroxyphenyl)methoxy]phenyl]methylene]-2-thioxo-4-thiazolidinone

EXAMPLE 28
Preparation of 5-[[3-[(4-acetyl-3-hydroxy-2-propylphenyl)methoxy]phenyl]methylene]-2-thioxo-4-thiazolidinone

EXAMPLE 29
Preparation of 5-[[4-[(3-hydroxy-2-propylphenyl)methoxy]phenyl]methylene]-2-thioxo-4-thiazolidinone

EXAMPLE 30
Preparation of 5-[[4-[(4-acetyl-3-acetoxy-2-propylphenoxy)methyl]phenyl]methylene]-2-thioxo-4-thiazolidinone Under a nitrogen atmosphere in a round bottom flask 4-[(4-acetyl-3-acetoxy-2-propylphenoxy)methyl]benzaldehyde (70 mg, 0.20 mmol) was dissolved in acetic acid (1 ml). To this solution was added sodium acetate (59 mg, 0.72 mmol) and then rhodanine (27.5 mg, 0.21 mmol). The reaction mixture was then heated to reflux and the progress of the reaction was monitored by thin layer chromatography.

After 26 hours of refluxing the reaction mixture was allowed to cool to 70° C. The precipitate was removed by filtration. The precipitate was triturated with ethyl ether and then filtered, followed by trituration with water, filtration, and washing with ethyl ether. The solvents were then removed in vacuo to yield 40 mg (43%) of the title product. mp 218°–221° C. NMR, FDMS.

Analysis for $C_{24}H_{23}NO_5S_2$: Theory: C, 61.39; H, 4.94; N, 2.98. Found: C, 60.62; H, 4.99; N, 2.67.

EXAMPLE 31
Preparation of 5-[[4-[(4-acetyl-3-methoxy-2-propylphenoxy)methyl]phenyl]methylene]-2-thioxo-4-thiazolidinone Under a nitrogen atmosphere in a round bottom flask 4-[(4-acetyl-3-methoxy-2-propylphenoxy)methyl] benzaldehyde (60 mg, 0.18 mmol) was dissolved in 1 ml of acetic acid while stirring. To this solution was added sodium acetate (53 mg, 0.65 mmol), followed by the addition of rhodanine (24.5 mg, 0.18 mmol). The reaction mixture was then heated to reflux and maintained at this temperature. The progress of the reaction was monitored by thin layer chromatography.

After about 29 hours of refluxing, the reaction mixture was allowed to cool to 70° C. and then poured into 5 ml of water while stirring. The round bottom flask was washed with 1 ml of acetic acid, the wash being poured into the water-based mixture. After a few minutes of stirring a precipitate formed. The precipitate was removed by filtration which was then washed with water. The precipitate was then dried in vacuo.

The dried powder was dissolved in hot ethanol (9 ml) and then allowed to cool. The precipitate was filtered and washed lightly with ethanol, followed by drying under vacuum to yield 20 mg (25%) of the title product. mp 200°–202° C. NMR.

Analysis for $C_{23}H_{23}NO_4S_2$: Theory: C, 62.56; H, 5.25; N, 3.17. Found: C, 62.42; H, 5.40; N, 3.10.

EXAMPLE 32
Preparation of 5-[[4-[(2-chloro-6-fluorophenyl)methoxy] phenyl]methylene]-2-thioxo-4-thiazolidinone Under a nitrogen atmosphere in a round bottom flask 4-[(2-chloro-6-fluorophenyl)methoxy]benzaldehyde (1.00 g, 3.78 mmol) was dissolved in acetic acid (19 ml). To this solution was added sodium acetate (1.08 g, 13.2 mmol) and then rhodanine (0.50 g, 3.75 mmol). The reaction mixture was then heated to reflux and maintained at this temeprature. The progress of the reaction was monitored by thin layer chromatography.

After 42 hours of refluxing, the reaction mixture was allowed to cool to 70° C. and the precipitate was removed by filtration. The precipitate was washed lightly with acetic acid and then triturated with ethyl ether. After filtration the precipitate was triturated with water, filtered, and washed with ethyl ether. The solvents were removed in vacuo to yield 0.75 g (52%) of the title product. mp 224°–226° C. NMR, FDMS.

Analysis for $C_{17}H_{11}ClFNO_2S_2$: Theory: C, 53.75; H, 2.92; N, 3.69. Found: C, 53.46; H, 2.99; N, 3.79.

EXAMPLE 33
Preparation of 5-[[4-[(2-chloro-6-fluorophenyl)methoxy] phenyl]methylene]-3-(N,N-dimethylamino)-2-thioxo-4-thiazolidinone

EXAMPLE 34
Preparation of 5-[[3-[[4-(t-butyl)phenyl]methoxy]phenyl] methylene]-2-thioxo-4-thiazolidinone In a one liter three-neck flak 3-hydroxybenzaldehyde (19.5 g, 160 mmol) was dissolved in 300 ml of ethanol. This solution was cooled to 7° C. and then sodium hydroxide (32 ml of a 5N solution, 6.4 g, 160 mmol), sodium iodide (8.98 g, 60 mmol), 4-(t-butyl)benzyl bromide (25 g, 110 mmol), and an additional 300 ml of ethanol, were added. This reaction mixture was stirred at the cooled temperature for about one hour and then stirred for about 48 hours at room temperature.

The reaction mixture was then added to ice water and the organic fraction was extracted into ethyl acetate. The ethyl acetate layer was then washed with water, extracted with 2N sodium hydroxide, washed again with water, and then dried over sodium sulfate. The solvents were removed in vacuo.

The concentrate was redissolved in 10% ethyl acetate in hexane, filtered, then chromatographed using 10% ethyl acetate in hexane, with 25% ethyl acetate in hexane as the eluent to yield 19.5 grams (66.1%) of 3-[4-(t-butyl) benzyloxy]benzaldehyde.

The 3-[4-(t-butyl)benzyloxy]benzaldehyde (2 g, 7.5 mmol) was coupled to rhodanine (1.19 g, 9 mmol) by reacting the two in the presence of sodium acetate (2.42 g, 29 mmol) and acetic acid. The mixutre was heated to reflux and then refluxed overnight.

The reaction was cooled and the yellow precipitate was collected by vacuum filtration. The residue was washed with acetic acid (4 times) and water (4 times) to yield 2.21 grams (77.2%) of the title product as a yellow crystalline solid. mp 207.5°–208.5° C. NMR, FDMS(M+) 383.

Analysis for $C_{21}H_{21}NO2S_2$: Theory: C, 65.77; H, 5.52; N, 3.65. Found: C, 65.96; H, 5.57; N, 3.63.

EXAMPLE 35
Preparation of 5-[[4-[(3-hydroxyphenyl)methoxy]phenyl] methylene]-2-thioxo-4-thiazolidinone

EXAMPLE 36
Preparation of 5-[[4-[[4-(t-butyl)phenyl]methoxy]phenyl] methylene]-2-thioxo-4-thiazolidinone In a one liter three-neck flask 4-hydroxybenzaldehyde (19.5 g, 160 mmol) was dissolved in 300 ml of ethanol. This solution was cooled to 8° C. and then sodium hydroxide (32 ml of a 5N solution, 6.4 g, 160 mmol), sodium iodide (8.98 g, 60 mmol), an additional 300 ml of ethanol, and 4-(t-butyl) benzyl bromide were added. This mixture was stirred for one hour at the cooled temperature and then stirred for about 48 hours at room temperature.

The reaction mixture was then added to ice water and the organic fraction was extracted into ethyl acetate. The ethyl acetate layer was then washed with water, extracted with 2N sodium hydroxide, washed with water, and then dried over sodium sulfate. The solvents were removed in vacuo.

Recrystallization from ethanol and subsequent vacuum filtration yielded 25.1 g (85.1%) of 4-[(4-t-butyl)benzyloxy] benzaldehyde.

The 4-[(4-t-butyl)benzyloxy]benzaldehyde (2.6 g, 9 mmol) was then coupled with rhodanine (1.4 g, 10.5 mmol) by adding the reactants to sodium acetate (2.9 g, 36 mmol) and acetic acid. The reaction mixture was then heated to reflux and refluxed overnight.

The reaction mixture was then cooled and the yellow-orange precipitate was collected by vacuum filtration and then washed with acetic acid (3 times) and then washed with water (4 times). mp 185°–186° C. NMR. FDMS (M+) 383.

Analysis for $C_{21}H_{21}NO_2S_2$: Theory: C, 65.77; H, 5.52; N, 3.65. Found: C, 66.00; H, 5.57; N, 3.50.

EXAMPLE 37
Preparation of 5-[[4-[(2,6-difluorophenyl)methoxy]phenyl] methylene]-2-thioxo-4-thiazolidinone

EXAMPLE 38
Preparation of 5-[[4-[(2-chlorophenyl)methoxy]phenyl]methylene]-2-thioxo-4-thiazolidinone

EXAMPLE 39
Preparation of 5-[[4-[(3,5-dimethoxyphenyl)methoxy]phenyl]methylene]-2-thioxo-4-thiazolidinone

EXAMPLE 40
Preparation of 5-[[4-[(2,5-dimethylphenyl)methoxy]phenyl]methylene]-2-thioxo-4-thiazolidinone

EXAMPLE 41
Preparation of 5-[[4-[(4-chlorophenyl)methoxy]phenyl]methylene]-2-thioxo-4-thiazolidinone Under a nitrogen atmosphere in a round bottom flask 4-[(4-chlorophenyl)methoxy]benzaldehyde (0.40 g, 1.62 mmol) was dissolved in acetic acid (8.1 ml) while stirring. To this solution was added sodium acetate (0.47 g, 5.7 mmol) followed by the addition of rhodanine (0.22 g, 1.65 mmol). The reaction mixture was heated to the reflux temperature and maintained at this temperature. The progress of the reaction was monitored by thin layer chromatography.

After 25 hours of refluxing the reaction mixture was allowed to cool to 70° C. and then filtered. The precipitate was washed lightly wtih acetic acid and then triturated in ethyl ether. After filtration, trituration with water, and subsequent refiltration, the precipitate was washed with ethyl ether. The solvents were removed in vacuo to yield 0.37 g (63%) of the title product. mp >225° C. FDMS.

Analysis for $C_{17}H_{12}ClNO_2S_2$: Theory: C, 56.43; H, 3.34; N, 3.87. Found: C, 56.63; H, 3.51; N, 4.02.

EXAMPLE 42
Preparation of 5-[[4-[(2-methylphenyl)methoxy]phenyl]methylene]-2-thioxo-4-thiazolidinone Analysis for $C_{18}H_{15}NO_2S_2$: Theory: C, 63.32; H, 4.43; N, 4.10. Found: C, 63.47; H, 4.64; N, 4.15.

EXAMPLE 43
Preparation of 5-[[4-[(naphth-1-yl)methoxy]phenyl]methylene]-2-thioxo-4-thiazolidinone Under a nitrogen atmosphere in a round bottom flask 4-[(naphth-1-yl)methoxy]benzaldehyde (5.25 g, 20 mmol) was dissolved in 100 ml of acetic acid. To this solution was added sodium acetate (5.74 g, 70 mmol) and rhodanine (2.66 g, 20 mmol). The reaction mixture was raised to the reflux temperature and maintained at this temperature. The progress of the reaction was monitored by thin layer chomratography.

After 47 hours of refluxing, the reaction mixture was allowed to cool to 70° C. The precipitate was removed by filtration and washed lightly with acetic acid. The precipitate was triturated with ethyl ether, filtered, triturated with water, and then filtered again and washed with ethyl ether. The solvents were removed in vacuo to yield 5.82 g (77%) of the title product. mp >225° C. FDMS.

Analysis for $C_{21}H_{15}NO_2S_2$: Theory: C, 66.82; H, 4.01; N, 3.71. Found: C, 67.03; H, 4.14; N, 3.87.

EXAMPLE 44
Preparation of 5-[[4-[(naphth-2-yl)methoxy]phenyl]methylene]-2-thioxo-4-thiazolidinone Under a nitrogen atmosphere in a round bottom flask 4-hydroxybenzaldehyde (8.57 g, 70.1 mmol) was dissolved in 102 ml of ethanol. This solution was cooled to 0C and then sodium hydroxide (13.6 ml of a 5N solution) and sodium iodide (4.77 g, 32 mmol) were added while stirring. To this mixture was then added 2-(bromomethyl) naphthalene (13.27 g, 60 mmol) and then stirred at 0° C. for about 30 minutes. The reaction mixture was then allowed to warm to room temperature and maintained at this temperature.

After 42 hours at room temperature, the reaction mixture was partitioned between ethyl acetate and water. The layers were separated and the organic fraction was extracted with 1N sodium hydroxide, followed by an extraction with a saturated sodium chloride solution. The organic fraction was dried over sodium sulfate and the solvents were removed in vacuo. The reaction products were dissolved in 50 ml of ethyl acetate over a steam bath and then 25 ml of hexane were added. The mixture was allowed to cool to room temperature and then filtered to remove the reaction products which were washed with hexane. The solvents were removed in vacuo to yield 10.86 g (69%) of 4-[(naphth-2-yl)methoxy]benzaldehyde. mp 103°–109° C.

Under a nitrogen atmosphere in a round bottom flask 4-[(naphth-2-yl)methoxy]benzaldehyde (5.24 g, 20 mmol) was dissolved in 100 ml of acetic acid. To this solution was added sodium acetate (5.74 g, 70 mmol) and rhodanine (2.66 g, 20 mmol). The reaction mixture was raised to the reflux temperature and maintained at this temperature. The progress of the reaction was monitored by thin layer chomratography.

After 30 hours of refluxing, the reaction mixture was allowed to cool to 70° C. The precipitate was removed by filtration and washed lightly with acetic acid. The precipitate was triturated with ethyl ether, filtered, triturated with water, and then filtered again and washed with ethyl ether. The solvents were removed in vacuo to yield 6.25 g (83%) of the title product. mp >225° C. FDMS.

Analysis for $C_{21}H_{15}NO_2S_2$: Theory: C, 66.82; H, 4.01; N, 3.71. Found: C, 67.08; H, 4.12; N, 3.90.

EXAMPLE 45
Preparation of 5-[[4-[(4-hexylphenyl)methoxy]phenyl]methylene]-2-thioxo-4-thiazolidinone Analysis for $C_{23}H_{25}NO_2S_2$: Theory: C, 67.12; H, 6.12; N, 3.80. Found: C, 66.84; H, 6.07; N, 3.13.

EXAMPLE 46
Preparation of 5-[[4-[(4-propylphenyl)methoxy]phenyl]methylene]-2-thioxo-4-thiazolidinone Analysis for $C_{20}H_{19}NO_2S_2$: Theory: C, 65.01; H, 5.18; N, 3.99. Found: C, 65.28; H, 5.28; N, 3.88.

EXAMPLE 47
Preparation of 5-[[4-[(3-phenylphenyl)methoxy]phenyl]methylene]-2-thioxo-4-thiazolidinone Under a nitrogen atmosphere in a round bottom flask 4-hydroxybenzaldehyde (7.14 g, 58.5 mmol) was dissolved in 85 ml of ethanol. The reaction mixture was cooled to 0° C. While stirring sodium hydroxide (11.3 ml of 5N solution), sodium iodide (3.98 g, 26.5 mmol), and 2-(bromomethyl) biphenyl (12.36 g, 50.0 mmol) were added sequentially. This mixture was stirred for 30 munites at room temperature. The reaction mixture was then allowed to warm to room temperature and maintained at this temperature.

After 42 hours at room temperature the raction mixture was partitioned between ethyl acetate and 1N sodium hydroxide. The organic fraction was extracted twice with brine, dried over sodium sulfate, and then dissolved in 100 ml ethyl ether and 100 ml of hexane and heated. The mixture was heated to boiling and the volume reduced to about 140 ml. The mixture was then allowed to cool to room temperature. The precipitate was removed by filtration and washed with ethyl ether to yield 11.46 (79%) of 4-[(3-phenylphenyl)methoxy]benzaldehyde, mp 81°–82.5° C.

Under a nitrogen atmosphere in a round bottom flask 4-[(3-phenylphenyl)methoxy]benzaldehyde (3.2 g, 10 mmol) was dissolved in acetic acid. To this solution, while stirring, were added sodium acetate (2.87 g, 35 mmol) and rhodanine (1.33 g, 10 mmol). This mixture was heated to reflux and maintained at this temperature. The progress of this reaction was monitored by thin layer chromatography.

After 52 hours of refluxing the reaction mixture was cooled to 70° C. and then poured into 200 ml of stirring ice water, resulting in the formation of a yellow precipitate. The precipitate was removed by filtration, washed with water and then dissolved in a 50:50 mixture of methylene chloride and chloroform. This organic mixture was then extracted with a saturated sodium bicarbonate solution followed by an extraction with 1N hydrochloric acid. The organic fraction was then dried over sodium sulfate and the solvents were removed in vacuo.

The solids were dissolved in 400 ml of ethanol over a steam bath and then this solution was allowed to cool to room temperature. The precipitate was removed by filtration and washed with hexane. The solvents were removed in vacuo to yield 3.04 g (75%) of the title product. mp 184°–186° C.

Analysis for $C_{23}H_{17}NO_2S_2$: Theory: C, 68.46; H, 4.25; N, 3.47. Found: C, 68.68; H, 4.38; N, 3.65.

EXAMPLE 48
Preparation of 5-[[3-[(4-benzoylphenyl)methoxy]phenyl]methylene]-2-thioxo-4-thiazolidinone In a two liter three-neck flask 4-methylbenzophenone (30 g, 152 mmol), benzoyl peroxide (4 g, 16.5 mmol) and 500 ml of carbon tetrachloride were admixed. To this mixture was added N-bromosuccinimide (22.6 g, 127 mmol) and additional benzoyl peroxide (4 g, 16.5 mmol) and carbon tetrachloride (300 ml). The reaction mixture was heated to reflux and refluxed for about 48 hours. The progress of the reaction was monitored by thin layer chromatography.

After refluxing, the reaction mixture was cooled and then filtered. The filtrate was vacuum concentrated to yield the desired intermediate, 4-benzoylbenzyl bromide.

In a one liter three-neck flask 3-hydroxybenzaldehyde (10.9 g, 90 mmol) was dissolved in 300 ml of ethanol. This solution was cooled to about 8° C. and then sodium hydroxide (15.6 ml of a 5N solution, 3.12 g, 78 mmol), sodium iodide (5.9 g, 40 mmol), 4-benzoylbenzyl bromide (21.6 g, 78 mmol), and an additional 300 ml of ethanol were added. The reaction mixture was stirred for an hour at 8° C. and then at room temperature for about 4 days.

The reaction mixture was then vacuum concentrated and then partitioned between water and ethyl acetate. The organic phase was washed with water and then dried over sodium sulfate. The solvents were removed in vacuo.

The residue was then dissolved in 25% ethyl acetate in hexane and then chromatographed, eluting with 25% ethyl acetate in hexane to yield 15.7 grams (63.8%) of 3-(4-benzoylbenzyloxy)benzaldehyde.

The 3-(4-benzoylbenzyloxy)benzaldehyde (2.0 g, 6.3 mmol) was coupled with rhodanine (1.06 g, 8.0 mmol) in the presence of sodium acetate (1.89 g, 22 mmol) and acetic acid (75 ml) essentially as previously described to yield 1.6 grams (59.0%) of the deisred title product. mp 212.5°–213.5° C. NMR. FDMS (M+) 431.

Analysis for $C_{24}H_{17}NO_3S_2$: Theory: C, 66.80; H, 3.97; N, 3.25. Found: C, 66.98; H, 4.06; N, 3.51.

EXAMPLE 49
Preparation of 5-[[4-[(4-phenylcarbonylphenyl)methoxy]phenyl]methylene]-2-thioxo-4-thiazolidinone In a two liter three-neck flask under a nitrogen atmosphere were added 4-methylbenzophenone (30 g, 152 mmol), benzoyl peroxide (4 g, 16.5 mmol) and carbon tetrachloride (500 ml). To this mixture N-bromosuccinimide (22.6 g, 127 mmol), 300 ml of carbon tetrachloride, and benzoyl peroxide (4 g, 16.5 mmol) were added. This reaction mixture was heated to reflux and refluxed for about 48 hours. The progress of the reaction was monitored by thin layer chromatography.

After refluxing, the reaction mixture was cooled and the precipitate was collected by vacuum filtration to afford the desired intermediate, 4-benzoylbenzyl bromide.

The 4-benzoylbenzyl bromide was then coupled to 4-hydroxybenzaldehyde by dissolving the 4-hydroxybenzaldehyde (10.9 g, 90 mmol) in 300 ml of ethanol. This solution was cooled to about 8.5° C. To this cooled solution were added sodium hydroxide (15.6 ml of a 5N solution, 3.12 g, 78 mmol), sodium iodide (5.9 g, 40 mmol), 4-benzoylbenzyl bromide (21.6 g, 78 mmol), and an additional 300 ml of ethanol.

The reaction mixture was then stirred for one hour at 8° C. and then allowed to warm at room temperature, where it stirred for about four days. After stirring the reaction mixture was concentrated in vacuo. The residue was then partitioned between water and ethyl acetate. The organic fraction was washed with water, followed by 1N sodium hydroxide, then water, and then dried over sodium sulfate. The solvents were removed in vacuo. Recrystallization for ethyl acetate/hexane yielded 19.8 grams (80.4%) of 4-(4-benzoylbenzyloxy)benzaldehyde.

The 4-(4-benzoylbenzyloxy)benzaldehyde was coupled with rhodanine to yield the title compound by admixing the 4-(4-benzoylbenzyloxy)benzaldehyde (2.09 g, 6.3 mmol) with rhodanine (1.0 g, 7.5 mmol), sodium acetate (1.8 g, 22 mmol) and acetic acid (75 ml) in a 250 ml flask. The reaction mixture was heated to reflux and refluxed overnight.

The reaction was cooled to room temperature and stirred at this time for about 24 hours. The precipitate was recovered by vacuum filtration which was then washed with acetic acid (3 times) and then water (3 times). The residue was triturated with hexane and then filtered to yield 1.27 grams (46.8%) of the title product. mp 252.5° C. NMR. FDMS (M+) 431.

Analysis for $C_{24}H_{17}NO_3S_2$: Theory: C, 66.80; H, 3.97; N, 3.25. Found: C, 66.48; H, 3.67; N, 3.65.

EXAMPLE 50
Preparation of 5-[[4-[[4-(1,1-dimethylprop-1-yl)phenoxy]methyl]phenyl]methylene]-2-thioxo-4-thiazolidinone

EXAMPLE 51
Preparation of 5-[[4-[(4-butylphenyl)methoxy]phenyl]methylene]-2-thioxo-4-thiazolidinone

EXAMPLE 52
Preparation of 5-[[3-[(4-butylphenyl)methoxy]phenyl]methylene]-2-thioxo-4-thiazolidinone

EXAMPLE 53
Preparation of 5-[[4-[(3-hexylphenyl)methoxy]phenyl]methylene]-2-thioxo-4-thiazolidinone Analysis for $C_{23}H_{25}NO_2S_2$: Theory: C, 67.12; H, 6.12; N, 3.80. Found: C, 67.34; H, 6.03; N, 3.31.

EXAMPLE 54
Preparation of 5-[[4-(4-hydroxymethylphenoxy)phenyl]methylene]-2-thioxo-4-thiazolidinone

EXAMPLE 55
Preparation of 5-[[3-[[3,5-di(t-butyl)-4-methoxyphenyl]methoxy]phenyl]methylene]-2-thioxo-4-thiazolidinone The title compound was prepared essentially as described in Example 56, infra, except that 3-hydroxybenzaldehyde was employed in place of the 4-hydroxybenzaldehyde. mp 239°–243° C. NMR, FDMS.

Analysis for $C_{26}H_{31}NO_3S_2$: Theory: C, 66.49; H, 6.65; N, 2.99. Found: C, 66.21; H, 6.65; N, 2.91.

EXAMPLE 56
Preparation of 5-[[4-[[3,5-di(t-butyl)-4-methoxyphenyl]methoxy]phenyl]methylene]-2-thioxo-4-thiazolidinone Under a nitrogen atmosphere in a three-neck round bottom flask 2,6-di(t-butyl)-4-methylphenol (55 g, 250 mmol) and methyl iodide (21.8 ml, 49.7 g, 500 mmol) were dissolved in 1.25 liters of tetrahydrofuran mixed with 125 ml of N,N-dimethylformamide. This solution was cooled to –5° C. and then sodium hydride (12 g, 500 mmol) was added over five minutes. The temperature of the reaction mixture was then allowed to rise to room temperature. The reaction mixture was stirred at room temperature for about six hours. Water (20 ml) was then slowly added and the volume was reduced to about 400 ml by distillation.

The insoluble inorganics were then removed by filtration. Ethyl acetate was then added and the precipitating inorganics were removed by filtration. The filtrate was washed four times with water, followed by a wash with brine. The organics were dried over sodium sulfate and the solvents were reduced in vacuo to yield 1,3-di(t-butyl)-2-methoxy-5-methylbenzene (57.2 g, 98%) as a yellow liquid.

The 1,3-di(t-butyl)-2-methoxy-5-methylbenzene is converted to 1,3-di(t-butyl)-2-methoxy-5-bromomethylbenzene by first dissolving the starting material (57.2 g, 244 mmol) in 1.58 liters of chloroform under a nitrogen purge, and then adding N-bromosuccinimide (47.8 g, 268 mmol) while stirring. Benzoyl peroxide (250 mg) was then added and the reacion mixture was refluxed for about two hours and then allowed to cool overnight after which time 2,2'-azobisisobutyronitrile (AIBN, 5.9 g) was added and the resulting mixture was refluxed for an additional two hours. The succinimide was removed by filtration and the solvents were removed in vacuo. The resulting residue was dissolved in 100 ml of hexane, filtered to remove inorganics, and recrystallized at –78° C. to yield 45.33 g (59%) of the intermediate 1,3-di(t-butyl)-2-methoxy-5-bromomethylbenzene.

Under a nitrogen atmosphere 1,3-di(t-butyl)-2-methoxy-5-bromomethylbenzene (6.26 g, 20 mmol) is then reacted with 4-hydroxybenzaldehyde (2.44 g, 20 mmol) and potassium carbonate (3.04 g) in 140 ml of methyl ethyl ketone. The reaction mixture is heated to reflux and maintained at this temperature for about 18 hours at which time the reaction mixture is cooled. The inorganics are removed by filtration and the filtrate is concentrated in vacuo. The concentrated reaction products are purified by silica gel chromatography to yield 5.8 grams (81%) of 4-[[3,5-di(t-butyl)-4-methoxyphenyl]methoxy]benzaldehyde.

In a round bottom flask under nitrogen purge 4-[[3,5-di(t-butyl)-4-methoxyphenyl]methoxy]benzaldehyde (530 mg, 1.5 mmol) is admixed with rhodanine (240 mg, 1.8 mmol) and sodium acetate (490 mg, 6.0 mmol) in 10 ml of acetic acid. The reaction mixture is then refluxed overnight with stirring. After the refluxing, the reaction mixture was allowed to cool to 70° C. The precipitate was removed by filtration and washed lightly with acetic acid. The precipitate was triturated with ethyl ether, filtered, triturated with water, and then filtered again and washed with ethyl ether. The solvents were removed in vacuo to yield 160 mg (23%) of the title product. mp 213°–218° C. NMR, FDMS.

Analysis for $C_{26}H_{31}NO_3S_2$: Theory: C, 66.49; H, 6.65; N, 2.99. Found: C, 66.23; H, 6.70; N, 3.07.

EXAMPLE 57
Preparation of 5-[[3-(4-pentylphenoxy)phenyl]methylene]-2-thioxo-4-thiazolidinone In a one three-neck flask were added 4-n-amyl phenol (20 g, 120 mmol), 3-bromobenzaldehyde (44.7 g, 242 mmol), pyridine (600ml), copper bronze (10 g, 150 mmol), copper chloride (4 g, 40 mmol), and potassium carbonate (44.4 g, 0.3 mole). The reaction mixture was heated to reflux and refluxed for about five days.

The reaction mixture was filtered and the filtrate was vacuum concentrated. The concentrate was partitioned between ice and ethyl acetate. The orgnic fraction was washed wtih water, extracted twice with 2N hydrochloric acid, washed with water, and then dried over sodium sulfate. The solvents were removed in vacuo.

The residue was dissolved in 10% ethyl acetate in hexane, filtered, then chromatographed using a gradient beginning with 10% ethyl acetate in hexane and concluding with 25% ethyl acetate in hexane to yield 3-(4-n-pentylphenoxy)benzaldehyde.

The 3-(4-n-pentylphenoxy)benzaldehyde was coupled with rhodanine in acetic acid and sodium acetate essentially as described previously to yield 1.3 grams (61.9%) of the title product. mp 125°–127° C. NMR. FDMS (M+) 383.

Analysis for $C_{21}H_{21}NO_2S_2$: Theory: C, 65.77; H, 5.52; N, 3.65. Found: C, 65.56; H, 5.57; N, 3.50.

EXAMPLE 53
Preparation of 5-[[4-[(2-benzylphenyl)methoxy]phenyl]methylene]-2-thioxo-4-thiazolidinone Under a nitrogen atmosphere in a round bottom flask 2-benzylbenzyl alcohol (14.8 g, 74.6 mmol) and 4-hydroxybenzaldehyde (10.38 g, 85.1 mmol) were dissolved in 75 ml of tetrahydrofuran. The reaction solution was then cooled to –20° C. To this solution diethyl azodicarboxylate (13.4 ml, 85 mmol), which had been admixed with triphenylphosphine (22.30 g, 85 mmol), and an additional 75 ml of tetrahydrofuran, was added dropwise at a rate which kept the temperature between –20° C. and –10° C. After the addition as complete the reaction mixture was allowed to warm to room temperature and then stirred for about 2½ hours at which time 0.48 ml of a 30% hydrogen peroxide solution was added. This was then stirred for about 15 minutes.

The reaction mixture was then partitioned between ethyl acetate and water, the organic fraction being further extracted with 1N sodium hydroxide and then brine. The organic fraction was dried over sodium sulfate and the solvents were removed in vacuo. The solids were dissolved in ethyl ether and hexane was added to precipitate. The precipitate was recovered by filtration and washed with ethyl ether. The solids were then dissolved in methylene chloride on a steam bath and the 4-[(2-benzylphenyl)methoxy]benzaldehyde were purified by silica gel chromatography, followed by removal of the solvents in vacuo, to yield 14.3 g (63%).

Under a nitrogen atmosphere in a round bottom flask 4-[(2-benzylphenyl)methoxy]benzaldehyde (4.5 g, 14.9 mmol), sodium acetate (4.27 g, 52 mmol), and rhodanine (1.98 g, 14.9 mmol) were dissolved in 75 ml of acetic acid. The reaction solution was then heated to reflux and maintained at this temperature for about three days.

After this reaction period the mixture was allowed to cool. The precipitate was removed by filtration, washed with acetic acid, triturated with ethyl ether, filtered, and then washed again with ethyl ether. This was then followed by trituration with water, followed by filtration, and washing with ethyl ether. The solvents were removed in vacuo to yield 5.39 g (87%) of the title product. mp 189°–192° C. FDMS.

Analysis for $C_{24}H_{19}NO_2S_2$: Theory: C, 69.04; H, 4.59; N, 3.35. Found: C, 69.24; H, 4.50; N, 3.62.

EXAMPLE 59
Preparation of 5-[[4-[(2-trifluoromethylphenyl)methoxy]phenyl]methylene]-2-thioxo-4-thiazolidinone Under a nitrogen atmosphere in a round bottom flask 2-trifluoromethylbenzyl alcohol (9.5 g, 53.9 mmol) and 4-hydroxybenzaldehyde (7.5 g, 61.5 mmol) were dissolved in 160 ml of tetrahydrofuran. The reaction solution was then cooled to −20° C. To this solution diethyl azodicarboxylate (9.67 ml, 62 mmol), which had been admixed with triphenylphosphine (16.11 g, 61.5 mmol), and an additional 54 ml of tetrahydrofuran, was added dropwise at a rate which kept the temperature between −20° C. and −10° C. After the addition as complete the reaction mixture was allowed to warm to room temperature and then stirred for about 2½ hours at which time 0.35 ml of a 30% hydrogen peroxide solution was added. This was then stirred for about 15 minutes.

The reaction mixture was then partitioned between ethyl acetate and water, the organic fraction being further extracted with 1N sodium hydroxide and then brine. The organic fraction was dried over sodium sulfate and the solvents were removed in vacuo. The solids were dissolved in ethyl ether and hexane was added to precipitate. The precipitate was recovered by filtration and washed with ethyl ether. The solids were then dissolved in methylene chloride on a steam bath and the 4-[(2-trifluoromethylphenyl)methoxy]benzaldehyde were purified by silica gel chromatography, followed by removal of the solvents in vacuo, to yield 11.15 g (74%).

Under a nitrogen atmosphere in a round bottom flask 4-[(2-trifluoromethylphenyl)methoxy]benzaldehyde (2.98 g, 10.63 mmol), sodium acetate (3.05 g, 37.2 mmol), and rhodanine (1.42 g, 10.7 mmol) were dissolved in 53 ml of acetic acid. The reaction solution was then heated to reflux and maintained at this temperature for about three days.

After this reaction period the mixture was allowed to cool to about 100° C. The precipitate was removed by filtration, washed with acetic acid, triturated with ethyl ether, filtered, and then washed again with ethyl ether. This was then followed by trituration with water, followed by filtration, and washing with ethyl ether. The solvents were removed in vacuo to yield 2.7 g (65%) of the title product. mp 194°–196° C.

Analysis for $C_{18}H_{12}F_3NO_2S_2$: Theory: C, 54.68; H, 3.06; N, 3.54. Found: C, 54.93; H, 3.36; N, 3.30.

EXAMPLE 60
Preparation of 5-[[4-[(3-propylphenyl)methoxy]phenyl]methylene]-2-thioxo-4-thiazolidinone Analysis for $C_{20}H_{19}NO_2S_2$: Theory: C, 65.01; H, 5.18; N, 3.79. Found: C, 65.22; H, 5.28; N, 3.66.

EXAMPLE 61
Preparation of 5-[[4-(4-pentylphenoxy)phenyl]methylene]-2-thioxo-4-thiazolidinone Preparation
Preparation of 4-(bromomethyl)benzaldehyde In a 5 lier three-neck flask under a nitrogen atmosphere methyl 4-(bromomethyl)benzoate (49.86 g, 217.7 mmol) was dissolved in 700 ml of toluene. The stirring solution was cooled via dry ice/acetone bath to an internal temperature of −78° C. before the dropwise addition of diisobutylaluminum hydride (600 ml of a 1.0M solution in toluene). The DIBAH was added at such a rate that the internal temperature never exceeded −70° C. The progress of the reaction was monitored by thin layer chromatography (silica; 10% ethyl acetate in hexane). To the stirring reaction mixture was slowly added 250 ml of methanol. The reaction mixture was then removed from the ice bath and allowed to warm to room temperature.

To this reaction mixture was then added water (500 ml), sodium potassium tartrate tetrahydrate (280 g) and ether (1.5 L) and the reaction was stirred at room temperature overnight. The phases were then separated and the aqueous fraction was extracted with ether (750 ml). The combined organic phases were washed with water (300 ml), followed by a wash with brine (300 ml) and then dried over magnesium sulfate. The solvents were removed in vacuo to yield 41.6 grams of white solid which was then dissolved in hot ether and then filtered. The ether filtrate was concentrated to about 250 ml on a steam bath and then solwly diluted with hexane to a final volume of about 350 ml. After another filtration, the filtrate was permitted to cool to room temperature.

The crystals which formed during the cooling period were collected and dried to yield 25.5 g (58.3%) of 4-bromomethylbenzyl alcohol as a crystalline solid. Additional amounts of this intermediate may be recovered from the mother liquor of the crystallization by silica gel chromatography.

The 4-bromomethylbenzyl alcohol (57.91 g, 288.0 mmol) was then converted to the corresponding aldehyde by dissolving the intermediate in 350 ml of dichloromethane and then adding this solution to a flask containing pyridinium chlorochromate (93.0 g, 431 mmol) suspended in 750 ml of dichloromethane. The dark-brown reaction mixture was then stirred at room temperature under nitrogen atmosphere. After 70 minutes of stirring most of the starting material had been consumed as determined by thin layer chromatography.

The reaction mixture was then filtered through a CELITE® pad and the filtrate was concentrated in vacuo. The residue was then partitioned between ether (1 L) and water (500 ml). The organic fraction was then washed with brine (250 ml) and then dried over magnesium sulfate. The solvents were removed in vacuo to yield 42.3 grams of white solid.

This white solid was dissovled in hot ether on the steam bath and filtered and the filtrate was concentrated to a volume of about 500 ml and permitted to cool slowly to room temperature. Th reaction vessel was then refrigerated overnight and the resulting crystals were then collected and dried in vacuo to yield 25.3 grams of the title product as a white solid. mp 97°–98° C.

Analysis for $C_8H_7BrO$: Theory: C, 48.27; H, 3.55; Br, 40.14. Found: C, 48.53; H, 3.51; Br, 40.02.

EXAMPLE 62
Preparation of 5-[[4-[(4-decanoyl-3-hydroxy-2-propylphenoxy)methyl]phenyl]methylene]-2-thioxo-4-thiazolidinone.

In a three-neck flask under a nitrogen atmosphere, 1,3-diethoxybenzene (13.29 g, 80.0 mmol) was dissolved in 400 ml of dry tetrahydrofuran. The stirring solution was cooled to −5° C. before the dropwise addition of n-butyl lithium (80.0 mmol) which had been dissolved in 50 ml of hexanes. During this dropwise addition, which took some twelve minutes, the temperature of the reaction mixture was maintained between −5° C. and 0° C. The reaction mixture was then stirred for about two hours in an ethanol/ice bath, the temperature of the reaction mixture being held below 15° C.

The reaction mixture was then cooled to −75° C. at which time 1-iodopropane (13.6 g, 80.0 mmol) was added dropwise. The reaction mixture was then stirred under nitrogen atmosphere in a dry ice/acetone bath for about 69 hours. Water (70 ml) was then added to the reaction flask and the stirring was continued at room temperature for about 20 minutes and then the contents were reduced in vacuo. The residue was partitioned between diethyl ether (250 ml) and water (100 ml). The organic phase was washed with water (3×50 ml), followed by a wash with brine (50 ml). The organic fraction was then dried over magnesium sulfate and the solvents were removed in vacuo. The desired intermediate was then further purified by silica gel chromatography to yield 10.67 g (64%) of 1,3-diethoxy-2-propylbenzene as a colorless oil.

The 1,3-diethoxy-2-propylbenzene was then converted to 1,3-dihydroxy-2-propylbenzene by reacting the intermediate produced supra (10.0 g, 48.0 mmol) with glacial acetic acid (500 ml) and hydrobromic acid (300 ml of a 48% aqueous solution) while stirring. The cloudy reaction solution was stirred while heating to reflux and was refluxed for 200 minutes. The reaction mixture was then allowed to cool to room temperature and the solvents were partially removed in vacuo before 500 ml of water was added. The resulting mixture was extracted with ether (2×500 ml) and the combined organic phases were washed with brine (100 ml) and then dried over sodium sulfate. The solvents were then removed in vacuo.

The desired intermediate, 1,3-dihydroxy-2-propylbenzene, was further purified by silica gel chromatography using a step gradient starting with 10% ethyl acetate in hexane and finishing with 15% ethyl acetate in hexane. The desired intermediate was then recrystallized from ether/hexane to yield 4.2 g (57%) product as colorless crystals.

The 1,3-dihydroxy-2-propylbenzene (4.07 g, 26.7 mmol) was then acylated by first dissolving it in dichloromethane (160 ml) under nitrogen atmosphere while stirring. This solution was cooled to 0C and then decanoyl chloride (11.0 ml, 53.0 mmol) was added to the above solution. To this stirring mixture was added portionwise aluminum chloride (3.7 g, 27.7 mmol). The reaciton mixture was then stirred at 0C for about one hour, by which time no starting material remained in the reaction vessel as determined by thin layer chromatography.

The reaction solution was then added to about 300 ml of ice and 40 ml of 5N hydrochloric acid. When all of the ice had melted, the mixture was extracted with ethyl acetate (350 ml). The organic phase was then washed with brine and dired over soldium sulfate. The solvents were removed in vacuo.

The residue was dissoved in 350 ml of ethanol and treated with 60 ml of 4N potassium hydroxide. This mixture was allowed to stir overnight at room temperature and then acidified by the addition of 50 ml of 5N hydrochloric acid. The mixture was concentrated in vacuo and extracted with ethyl acetate (100 ml). The orgnic phase was washed with brine and then dried over magnesium sulfate. The solvents were removed in vacuo. The residue was then dissolved in a minimum amount of ethyl acetate and the desired intermediate, 1,3-dihydroxy-2-propyl-4-decanoylbenzene (2.75 g, 34%), was recrystallized from hot hexane as colorless needles.

The 1,3-dihydroxy-2-propyl-4-decanoylbenzene (2.20 g, 7.2 mmol) thus obtained was coupled with 4-(bromomethyl) benzaldehyde (1.50 g, 7.5 mmol) by first dissolving the 1,3-dihydroxy-2-propyl-4-decanoylbenzene in about 5 ml of dry N,N-dimethylformamide. To this solution were then added N,N-dimethylformamide (95 ml), potassium carbonate (1.0 g, 7.2 mmol), potassium iodide (1.24 g, 7.5 mmol), and the benzaldehyde. The stirring reaction mixture was then heated to about 70° C. under a nitrogen atmosphere and maintained at this temperature for about 25 hours.

The reaction mixture was then allowed to cool to room temperature and was then added to 400 ml of water and then extracted with ethyl acetate (2×100 ml). The organic fractions were combined and then washed with water (100 ml) then brine (50 ml) and then dried over magnesium sulfate. The solvents were removed in vacuo, resulting in 3.77 g of a yellow solid. This solid was then dissolved in hot ether and filtered on a steam bath. The filtrate was then concentrated on the steam bath to about 25 ml and hexane was slowly added to 50 ml of total volume. The mixture was then allowed to cool to room temperature and then refrigerated. The resulting crystals were collected and dried to leave 1.70 g (56%) of the desired intermediate, 4-[(4-decanoyl-3-hydroxy-2-propylphenoxy)methyl]benzaldehyde, as a pale yellow material.

The 4-[(4-decanoyl-3-hydroxy-2-propylphenoxy)methyl] benzaldehyde thus obtained was coupled with the rhodanine by reacting equimolar amounts of the benzaldehyde and the rhodanine in the presence of sodium acetate and acetic acid as previously described to yield 1.6 g (84%) of the title product. mp 187.5°–188° C.

Analysis for $C_{20}H_{19}NO_2S_2$: Theory: C, 66.76; H, 6.91; N, 2.60. Found: C, 67.01; H, 6.66; N, 2.61.

EXAMPLE 63

Preparation of 5-[[4-[4-(t-butyl)phenylthio]phenyl]methylene]-2-thioxo-4-thiazolidinone In a two liter three-neck flask were added 4-t-butylthiophenol (17.8 g, 107 mmol), 4-bromobenzaldehyde (383.8 g, 210 mmol), copper bronze (19.1 g, 300 mmol), copper chloride (9 g, 90 mmol), potassium carbonate (44.9 g, 300 mmol) and pyridine (600 ml). This mixture was heated to reflux and then refluxed for about six days.

After the refluxing the reaction mixture was filtered hot and the filtrate was concentrated in vacuo. The concentrate was partitioned between ethyl acetate, water, and 5N hydrochloric acid. The organic fraction was washed with water, extracted wtih 2N sodium hydroxide, then washed with water, and then dried over sodium sulfate. The solvents were removed in vacuo.

The residue was dissolved in hexane and chromatographed with a gradient of hexane, 1% ethyl acetate in hexane, and 10% ethyl acetate in hexane to yield the deisred intermediate 4-[4-(t-butyl)phenylthio]benzaldehyde.

The 4-[4-(t-butyl)phenylthio]benzaldehyde (1.5 g, 5.5 mmol) was coupled with rhodanine (0.87 g, 6.5 mmol) in the presence of sodium acetate (1.64 g, 20 mmol) and acetic acid (80 ml) essentially as previously described to yield 1.1 grams (52.3%) of the title product. mp 211°–212° C. NMR. FDMS (M+) 385.

Analysis for $C_{20}H_{19}NOS_3$: Theory: C, 62.30; H, 4.97; N, 3.63. Found: C, 62.24; H, 5.11; N, 3.64.

EXAMPLE 64

Preparation of 5-[[3-[4-(t-butyl)phenylthio]phenyl]methylene]-2-thioxo-4-thiazolidinone In a two liter three-neck flask 4-(t-butyl)thiophenol (17.3 g, 104 mmol), 3-bromobenzaldehyde (38.8 g, 210 mmol), copper bronze (19.05 g, 300 mmol), copper chloride (9 g, 90 mmol), potassium carbonate (41.4 g, 300 mmol) and 750 ml of pyridine were admixed and then heated to reflux and maintained at this temperature. The progress of the reaction was monitored by thin layer chromatography. After refluxing for six days the reaction mixture was filtered hot and the filtrate was concetrated in vacuo.

The concentrate was partitioned between ice, 5N hydrochloric acid, and ethyl acetate. The organic phase was washed wtih water, extracted with 2N sodium hydroxide, then water, and then dried. The solvents were removed in vacuo.

The residue was dissolved in hexane, filtered, and chromatographed with a gradient ranging from 1% to 5% ethyl acetate in hexane to yield 4-[4-(t-butyl)phenylthio] benzaldehyde.

The 4-[4-(t-butyl)phenylthio]benzaldehyde (1.5 g, 5.5 mmol) was condensed with rhodanine (0.865 g, 6.5 mmol) using sodium acetate (1.64 g, 20 mmol) and acetic acid (80 ml) essentially as previously described to yield 1.4 grams (66.7%) of the title compound. mp 188.5°–189.5° C. NMR. FDMS (M+) 385.

Analysis for $C_{20}H_{19}NOS_3$: Theory: C, 62.30; H, 4.97; N, 3.63. Found: C, 62.56; H, 5.04; N, 3.54.

EXAMPLE 65
Preparation of 5-[[4-[[3-(1-hydroxypent-1-yl)phenyl]methoxy]phenyl]methylene]-2-thioxo-4-thiazolidinone Analysis for $C_{23}H_{25}NO_3S_2$: Theory: C, 64.61; H, 5.89; N, 3.28. Found: C, 64.41; H, 5.85; N, 3.19.

EXAMPLE 66
Preparation of 5-[[4-[(2-hexylphenyl)methoxy]phenyl] methylene]-2-thioxo-4-thiazolidinone Analysis for $C_{23}H_{25}NO_2S_2$: Theory: C, 67.12; H, 6.12; N, 3.80. Found: C, 65.94; H, 6.00; N, 3.30.

EXAMPLE 67
Preparation of 5-[[3-[(4-butoxyphenyl)methoxy]phenyl] methylene]-2-thioxo-4-thiazolidinone

EXAMPLE 68
Preparation of 5-[[4-[(4-butoxyphenyl)methoxy]phenyl] methylene]-2-thioxo-4-thiazolidinone

EXAMPLE 69
Preparation of 5-[[4-[[2-(2-carboxyphenyl)phenyl)methoxy] phenyl]methylene]-2-thioxo-4-thiazolidinone Under a nitrogen atmosphere in a round bottom flask 2-(2-carboxyphenyl)benzyl alcohol (0.46 g, 2.02 mmol) was dissolved in 60 ml of ethyl acetate. This solution was stirred at room temperature as 9-fluorenone hydrazone (0.49 g, 2.52 mmol) dissolved in 10 ml of ethyl acetate was added dropwise over fifteen minutes. The progress of the reaction was monitored by thin layer chromatography. This mixture was then stirred at room temperature overnight at which time another 0.25 g (0.50 mmol) of 9-fluorenone hydrazone was added. This mixture was then stirred overnight.

The solvents were then removed in vacuo and the resulting solid was dissolved in ethyl acetate. This solution was then extracted with a saturated sodium bicarbonate solution, extracted with brine, and dried over sodium sulfate. The solvents were then removed in vacuo. The desired product was further purifed by by silica gel chromatography after dissolving the solids in toluene to give 0.65 g (81%) of the desired intermediate 2-[2-(1,1-diphenylmethoxycarbonyl) phenyl]benzyl alcohol.

Under a nitrogen atomsphere 2-[2-(1,1-diphenylmethoxycarbonyl)phenyl]benzyl alcohol (0.64 g, 1.62 mmol) was dissolved in 4.9 ml of tetrahydrofuran. The resulting solution was stirred at room temperature and then 4-hydroxybenzaldehyde (0.23 g, 1.89 mmol) and triphenylphosphine (0.48 g, 1.83 mmol) were then added. Under continued stirring the reaction vessel was cooled to –20° C. and a mixture of tetrahydrofuran (1.6 ml) and diethyl azodicarboxylate (0.29 ml, 1.84 mmol) were then added dropwise over about ten minutes. After the addition was complete the reaction mixture was allowed to cool to room temperature and maintained at thistemperature for about four hours. To this reaction mixture was then added 0.1 ml of 30% hydrogen peroxide. This resulting mixture was stirred for about fifteen minutes.

The reaction mixture was then diluted with ethyl ether and extracted with water, followed by extractions with 1N sodium hydroxide, then brine. The organic fraction was dried over sodium sulfate and the solvents were removed in vacuo. The desired product was further purifed by trituration with toluene followed by liquid chromatography to yield 0.58 g (72%) of the desired intermediate 4-[2-[2-(1,1-diphenylmethoxycarbonyl)phenyl]benzoxy]benzaldehyde.

The 4-[2-[2-(1,1-diphenylmethoxycarbonyl)phenyl] benzoxy]benzaldehyde was converted to the title product by first dissolving the intermediate (93.0 mg, 0.187 mmol) in 3.7 ml of methanol under a nitrogen atmosphere. While stirring 0.11 ml of 5N sodium hydroxide was added dropwise. This mixture was then stirred overnight at room temperature. The progress of the reaction was monitored by thin layer chromatography. Additional 4-[2-[2-(1,1-diphenylmethoxycarbonyl)phenyl]benzoxy]benzaldehyde (74.8 mg, 0.15 mmol) and methanol (3 ml) were added, followed by the dropwise addition of an additional 0.089 ml of the sodium hydroxide. The resulting mixture was heated to reflux and maintained at this temperature for about 22 hours. After the 22 hours, while still refluxing, 4.2 ml of water was added dropwise. After an additional 2.5 hours of refluxing the mixture was allowed to cool and the residual methanol was removed by evaporation. The resulting mixture was then partitioned between ethyl acetate and sodium bicarbonate. The organic fraction was collected and extracted twice with a saturated sodium bicarbonate solution. The organic fraction was then dried over sodium sulfate.

Fresh ethyl acetate was added to the combined aqueous fractions which were then acidified to pH 2.2 with 1N hydrochloric acid while stirring. The layers were separated and the aqueous fraction was extracted with ethyl acetate. The organic fraction was dried over sodium sulfate and combined with the above organic fraction to yield 102.8 mg (92%) of the desired intermediate 4-[2-(2-carboxyphenyl) benzoxy]benzaldehyde.

The 4-[2-(2-carboxyphenyl)benzoxy]benzaldehyde (93.7 mg, 0.28 mmol) was then coupled with rhodanine (37.5 mg, 0.28 mmol) as described supra to yield the title product (99.1 g, 79%). mp >225° C.

Analysis for $C_{24}H_{17}NO_4S_2$: Theory: C, 64.41; H, 3.83; N, 3.13. Found: C, 64.19; H, 4.02; N, 3.30.

EXAMPLE 70
Preparation of 5-[[4-[4-(t-butyl)phenyl]phenyl]methylene]-2-thioxo-4-thiazolidinone

EXAMPLE 71
Preparation of 5-[[4-[4-(t-butyl)phenoxy]phenyl]methylene] -2-thioxo-4-thiazolidinone

EXAMPLE 72
Preparation of 5-[[4-[3-(1-hydroxypropylphenyl)methoxy] phenyl]methylene]-2-thioxo-4-thiazolidinone

EXAMPLE 73
Preparation of 5-[[4-[(4-bromophenyl)methoxy]phenyl] methylene]-2-thioxo-4-thiazolidinone. NMR, mp 248°–251° C.

Analysis of $C_{17}H_{12}BrNO_2S_2$: Theory: C, 50.25; H, 2.98; N, 3.45. Found: C, 50.41; H, 3.10; N, 3.61.

EXAMPLE 74
Preparation of 5-[[4-[(2-bromophenyl)methoxy]phenyl] methylene]-2-thioxo-4-thiazolidinone. NMR, mp 219°–222° C.

Analysis of $C_{17}H_{12}BrNO_2S_2$: Theory: C, 50.25; H, 2.98; N, 3.45. Found: C, 50.12; H, 3.02; N, 3.31.

EXAMPLE 75
Preparation of 5-[[4-[(3-bromophenyl)methoxy]phenyl] methylene]-2-thioxo-4-thiazolidinone. mp 189°–193° C.

Analysis of $C_{17}H_{12}BrNO_2S_2$: Theory: C, 50.25; H, 2.58; N, 3.45. Found: C, 50.35; H, 3.08; N, 3.21.

EXAMPLE 76
Preparation of 5-[[4-[(2-iodophenyl)methoxy]phenyl] methylene]-2-thioxo-4-thiazolidinone. mp 225°–228° C.

Analysis of $C_{17}H_{12}INO_2S_2$: Theory: C, 45.04; H, 2.67; N, 3.09. Found: C, 45.15; H, 2.71; N, 3.09.

EXAMPLE 77
Preparation of (Z)-5-[[4-[(4-phenylcarbonyl-3-hydroxy-2-propylphenoxy)methyl]phenyl]methylene]-2-thioxo-4-thiazolidinone In a 500 ml, three-neck round bottom flask under a nitrogen atmosphere, 4-(bromomethyl)benzaldehyde (3.20 g, 12.5 mmol), (2,4-dihydroxy-3-propylphenyl) phenylmethanone (3.20 g, 12.5 mmol), potassium carbonate (1.71 g, 12.4 mmol), and potassium iodide (2.11 g, 12.7 mmol) were added to 160 ml of methyl ethyl ketone. The stirring reaction mixture was heated to reflux and maintained at reflux for 7.5 hours. The progress of the reaction was monitored by thin layer chromatography.

The reaction mixture was then allowed to cool to room temperature and was then concentrated in vacuo. The residue was partitioned between 150 ml of ethyl acetate and 100 ml of water. The aqueous phase was extracted with ethyl acetate (75 ml) and the organic phases were then combined, washed with water (100 ml) and then brine (75 ml) and then dried over magnesium sulfate. The solvents were removed in vacuo to yield 5.27 g of 4-[[(3-hydroxy-4-phenylcarbonyl-2-propyl)phenoxy]methyl]benzaldehyde as a reddish-brown oil. This oil was then dissolved in ethyl acetate and further purified by silica gel chromatography. The eluate was then dissolved in warm benzene, filtered, and the filtrate was concentrated over a steam bath. The residue was then diluted with hexane and heated over a steam bath. The solution was then allowed to cool to room temperature, followed by refigeration overnight to yield 1.098 g (25% yield) of the intermediate 4-[[(3-hydroxy-4-phenylcarbonyl-2-propyl) phenoxy]methyl]benzaldehyde as fine yellow crystals.

Condensation of the above prepared intermediate (0.90 g, 2.4 mmol) with rhodanine (0.37 g, 2.8 mmol) was performed in sodium aceate and acetic acid essentially as described previously to yield 0.99 grams (84% final step yield) of the title product as a bright yellow powder. mp 229°–230° C.

Analysis of $C_{27}H_{23}NO_4S_2$: Theory: C, 66.24; H, 4.73; N, 2.86. Found: C, 66.51; H, 4.86; N, 2.87.

EXAMPLE 78
Preparation of 5-[[3-[[4-(t-butyl)phenyl]sulfonyl]phenyl] methylene]-2-thioxo-4-thiazolidinone

EXAMPLE 78
Preparation of 5-[[3-[[4-(t-butyl)phenyl]sulfinyl]phenyl] methylene]-2-thioxo-4-thiazolidinone

EXAMPLE 79
Preparation of 5-[[4-[[4-(t-butyl)phenyl]amino]phenyl] methylene]-2-thioxo-4-thiazolidinone

EXAMPLE 80
Preparation of 5-[[3-[[4-(t-butyl)phenyl]thiomethyl]phenyl] methylene]-2-thioxo-4-thiazolidinone

EXAMPLE 81
Preparation of 5-[[2-[4-(t-butyl)phenoxy]phenyl]methylene] -2-thioxo-4-thiazolidinone

EXAMPLE 82
Preparation of (Z)-5-[[4-[(4-phenylcarbonylphenoxy) methyl]phenyl]methylene]-2-thioxo-4-thiazolidinone In a 500 ml, three-neck round bottom flask under a nitrogen atmosphere, 4-(bromomethyl)benzaldehyde (4.02 g, 20.2 mmol), 4-hydroxybenzophenone (3.90 g, 19.7 mmol), potassium carbonate (2.76 g, 20.0 mmol), and potassium iodide (3.32 g, 20.0 mmol) were added to 200 ml of methyl ethyl ketone. The stirring reaction mixture was heated to reflux and maintained at reflux for 4 hours forty minutes. The progress of the reaction was monitored by thin layer chromatography.

The reaction mixture was then allowed to cool to room temperature and was then concentrated in vacuo. The residue was partitioned between 250 ml of ethyl acetate and 150 ml of water. The aqueous phase was extracted with ethyl acetate (75 ml) and the organic phases were then combined, washed with water (150 ml) and then brine (100 ml) and then dried over magnesium sulfate. The solvents were removed in vacuo to yield 9.67 g of 4-[[4-(phenylcarbonyl) phenoxy]methyl]benzaldehyde as a yellow powder.

This powder was then dissolved in warm ethyl acetate and then allowed to cool to room temperature, followed by refigeration overnight to yield 3.04 g (49% yield) of the intermediate 4-[[4-(phenylcarbonyl)phenoxy]methyl] benzaldehyde as fine yellow crystals.

Condensation of the above prepared intermediate (2.80 g, 8.85 mmol) with rhodanine (1.27 g, 9.53 mmol) was performed in sodium aceate and acetic acid essentially as described previously to yield 2.52 grams (66% final step yield) of the title product as a lemon yellow crystalline solid. mp 244°–246° C.

Analysis of $C_{24}H_{17}NO_3S_2$: Theory: C, 66.80; H, 3.97; N, 3.25. Found: C, 66.71; H, 4.01; N, 3.15.

EXAMPLE 83
Preparation of 5-[[4-[[2-(2-phenyleth-1-yl)phenoxy]methyl] phenyl]methylene]-2-thioxo-4-thiazolidinone In a 250 ml, three-neck round bottom flask, under a nitrogen atmosphere, 2-phenethylbenzyl alcohol (4.25 g, 20.0 mmol), 4-hydroxybenzaldehyde (2.56 g, 21.0 mmol), and triphenylphosphine (5.50 g, 21.0 mmol) were dissolved in 30 ml of dry tetrahydrofuran. The reaction solution was then cooled to –1° C. before the dropwise addition of diethyl azodicarboxylate (3.50 g, 20.1 mmol) dissolved in 10 ml of dry tetrahydrofuran. The diethyl azodicarboxylate solution was added at such a rate that the temperature of reaction mixture never exceeded 4° C. Upon completion of the diethyl azodicarboxylate solution, the reaction mixture was allowed to warm to room temperature and was stirred at this temperature for about 72 hours. The progress of the reaction was monitored by thin layer chromatography.

The reaction mixture was then concentrated in vacuo and then 10 ml of chloroform was added to the residue. The suspension was the filtered and the filtrate was further purified by silica gel cartridge chromatography, eluting with 10% ethyl acetate in hexane. Recrystallization yielded 2.44 grams of the intermediate 4-[2-(phenethyl)benzyloxy] benzaldehyde.

Condensation of the above prepared intermediate (0.80 g, 2.5 mmol) with rhodanine (0.38 g, 2.9 mmol) was performed in sodium aceate and acetic acid essentially as described previously to yield 0.431 grams (40% final step yield) of the title product as a bright yellow flocculent crystal solid. mp 162°–163° C.

Analysis of $C_{25}H_{21}NO_2S_2$: Theory: C, 69.58; H, 4.90; N, 3.24. Found: C, 69.63; H, 4.99; N, 3.31.

EXAMPLE 84
Preparation of 5-[[3-[4-(t-butyl)-2-propylphenoxy]phenyl] methylene]-2-thioxo-4-thiazolidinone

EXAMPLE 85
Preparation of 5-[[4-[[4-(t-butyl)-2-propylphenoxy]methyl] phenyl]methylene]-2-thioxo-4-thiazolidinone

EXAMPLE 86
Preparation of 5-[[3-[[4-(t-butyl)phenyl]amino]phenyl] methylene]-2-thioxo-4-thiazolidinone

EXAMPLE 87
Preparation of 5-[[4-[(3,4-dichlorophenyl)methoxy]phenyl] methylene]-2-thioxo-4-thiazolidinone

EXAMPLE 88
Preparation of 5-[[4-[2-(2-phenyloxazol-4-yl)ethoxy] phenyl]methylene]-2-thioxo-4-thiazolidinone. NMR, mp >220° C.

Analysis of $C_{21}H_{16}N_2O_3S_2$: Theory: C, 61.75; H, 3.95; N, 6.86. Found: C, 61.77; H, 4.04; N, 6.64.

EXAMPLE 89
Preparation of 5-[[4-[2-(2-phenyloxazol-4-yl)ethoxy] phenyl]methylene]-3-methyl-2-thioxo-4-thiazolidinone. mp 194°–200° C.

Analysis of $C_{22}H_{18}N_2O_3S_2$: Theory: C, 62.54; H, 4.29; N, 6.63. Found: C, 62.73; H, 4.28; N, 6.70.

EXAMPLE 90
Preparation of 5-[[4-[2-(2-phenyloxazol-4-yl)ethoxy] phenyl]methylene]-3-(N,N-dimethylamino)-2-thioxo-4-thiazolidinone In a two liter flask N,N-dimethylhydrazine (390 ml, 5.13 mol) was dissolved in 390 ml of ethanol and chilled with stirring to −3° C. A solution of carbon disulfide (134 ml, 2.22 mol) dissolved in ethyl ether was solowly added to the N,N-dimethylhydrazine solution, the addition taking over thirty minutes with stirring. After the addition was complete the resulting mixture was allowed to stir for about ten minutes then allowed to sit at ambient temperature for about three hours. The mixture was then filtered and the precipitate was washed with ethyl ether.

In a separate flask chloroacetic acid (161.7 g, 1.71 mol) was dissolved in 340 ml of 5N sodium hydroxide and 150 ml of water, the aqueous solutions being kept in an ice bath such that the temperature remained between 10° C. and 25° C. The above-purified solid was then added to this solution while stirring for about 45 minutes. The pH of the solution was then adjusted to pH 4.0 by the addition of concentrated hydrochloric acid (about 150 ml added), the solution being cooled so as to never exceed 35° C. The precipitate was then removed by filtration and washed with water to give 279.9 g (84%) of the opened ring analog of 3-(N,N-dimethylamino)-2-thioxo-4-thiazolidinone after drying.

Analysis of $C_{23}H_{21}N_3O_3S_2$: Theory: C, 59.56; H, 4.05; N, 9.92. Found: C, 59.55; H, 4.14; N, 9.62.

EXAMPLE 91
Preparation of 5-[[4-[2-[2-[3,5-di(t-butyl)-3-hydroxyphenyl]oxazol-4-yl]ethoxy]phenyl]methylene]-3-methyl-2-thioxo-4-thiazolidinone. mp 203°–204° C.

Analysis of $C_{30}H_{34}N_2O_4S_2$: Theory: C, 65.43; H, 6.22; N, 5.09. Found: C, 65.38; H, 6.34; N, 5.07.

EXAMPLE 92
Preparation of 5-[[4-[2-[2-[3,5-di(t-butyl)-3-hydroxyphenyl]oxazol-4-yl]ethoxy]phenyl]methylene]-2-thioxo-4-thiazolidinone. mp 217°–218° C.

Analysis of $C_{29}H_{32}N_2O_4S_2$: Theory: C, 64.90; H, 6.01; N, 5.22. Found: C, 64.81; H, 5.84; N, 5.04.

EXAMPLE 93
Preparation of 5-[[4-[2-[2-phenyloxazol-4-yl]ethoxy] phenyl]methylene]-3-amino-2-thioxo-4-thiazolidinone In another embodiment this invention describes methods for the treatment or prevention of Alzheimer's disease in a mammal which comprises administering to a mammal in need thereof an effective amount of a compound of Formula I or a pharamaceutically acceptable salt thereof. The biological activity of the compounds desbribed infra was evaluated using a variety of assay methods.

First, test compounds which inhibit exemplary aspartyl proteases, particularly cathepsin D, are identified as aspartyl protease inhibitors. As used herein, the term "test system" refers to an assay that is designed to measure aspartyl protease inhibitory activity. A typical test system used for such identification is a non-cellular assay where turnover of the protease substrate is monitored upon the administering of a protease inhibitor. The turnover of the protease inhibitor is then compared to the turnover of substrate in a control test system in which no such aspartyl protease inhibitor has been administered. As used herein, the term "control test system" refers to an identical test system that is run side-by-side with the test system with the exception no aspartyl protease inhibitor is administered. This non-cellular assay is used to identify those test compounds having suitable aspartyl protease inhibitory activity in a non-cellular environment.

An example of a non-cellular assay that may be used to determine in vitro aspartyl protease inhibitory activity reacts partially purified human brain cathepsin D with a substrate, e.g., porcine renin tetradecapeptide. The resultant reaction mixture is divided into portions and each portion is incubated for a different period of time. After the reaction is stopped, the turnover of substrate in each portion is determined using reverse-phase high performance liquid chromatography (HPLC). Protease inhibition activity may be calculated based on the rates of substrate turnover. This assay is exemplified in Assay 1, below.

A second non-cellular assay for determining in vitro aspartyl protease inhibitory activity utilizes a microtiter plate, where a suitable aspartyl protease, such as a cathepsin D is added to each well together with controls. A suitable fluorometric substrate is added to each well. The resultant reaction mixture is allowed to react for a preselected time, e.g., 30 minutes. After enzyme activity is terminated, the substrate or its product may be determined fluorometrically and then the protease inhibition activity may be calculated based on the rates of substrate turnover. This assay is exemplified in Assay 2, below.

A third non-cellular assay for determining in vitro aspartyl protease inhibitory activity which measures the hydrolysis of the test compound is described in B. M. Dunn, et al.,

*Journal of Biochemistry*, 237:899–906 (1986). This assay is carried out by incubating a test compound with a suitable aspartyl protease, such as cathepsin D, in a buffer. After an appropriate period of time, the hydrolysis of the test compound is quantified using reverse phase HPLC and amino acid hydrolysis. Then, stock solutions of the test compound are prepared at concentrations ranging from 1.0 to 5.0 mg/ml, and then 50–100 ml portions of these stock solutions were further diluted for rate determinations. The rate of hydrolysis is monitored by observing the decrease in the absorbance at 300 nm ($A_{300}$) These rates permit the calculation of $K_m$ and the percent inhibition of aspartyl protease. This assay is exemplfied in Assay 3.

It will be desirable to select those test compounds having aspartyl protease inhibitory activity for further testing in a cellular environment in order to identify which aspartyl protease inhibitors are most suitable for use as β-amyloid peptide production inhibitors. The initial assessment of aspartyl protease inhibitory activity may be based on a relative ranking of those test compounds tested, but will more typically be based on an absolute assessment of inhibitory activity, typically involving the measurement of an inhibitory concentration, i.e., the concentration needed to reach an arbitrary level of aspartyl protease inhibition, such as 50%. The term "$IC_{50}$" refers to the concentration needed to reach 50% inhibition.

Such $IC_{50}$ values can be measured using either of the above protocols by first determining the aspartyl protease activity in the absence of potential protease inhibitors in order to determine a control value. The aspartyl protease activity is then measured in the presence of varying concentrations of each test compound, and the concentration which results in an inhibition of protease activity of 50% is the $IC_{50}$ value. All test compounds which result in an $IC_{50}$ value at or below a selected threshold value may be designated suitable aspartyl protease inhibitors and may be further tested according to the methods of the present invention. This threshold value is arbitrary, but will usually be a low concentration, typically below 10 µg/ml, more usually 5 µg/ml, often 1 µg/ml, and sometimes 250 ng/ml, or below.

Assay 1

CATHEPSIN D INHIBITION ACTIVITY (NON-CELLULAR ASSAY)

Human brain cathepsin D was purified from frozen postmortem cortex substantially in accordance with the method of Nixon and Morotta, (1984) J. Neurochem. 43:507–516. The cortex material was prepared and applied to a DEAE-Sepharose® column. The flow through fraction was dialyzed against 50 mM Tris-HCl, pH 7.5, and applied to concanavalin A Sepharose® and eluted with 50 mM Tris, pH 7.5, 0.5M methyl α-D-mannopyranoside. The eluted cathepsin D activity was dialyzed against 25 mM Tris, pH 7.5, and stored at −40° C. (Con A pool) until use.

For each assay, 50 µl of the Con A pool was diluted to 270 µL in 200 mM sodium citrate, pH 4.5, 150 mM sodium chloride (NaCl), and incubated for 10 minutes at 4° C. with 15 µl of compound stock diluted in dimethylsulfoxide (DMSO). The substrate, a porcine renin tetradecapeptide, was added to each reaction mixture to yield a final concentration of 44 µM in a total volume of 300 µL. The samples were incubated at 37° C. for 0, 10, 20, or 30 minutes, and then boiled for 5 minutes to stop the reaction. The samples were centrifuged in a microcentrifuge for 10 minutes at 14,000 rpm at 4° C. After centrifugation, 200 µL of each reaction was injected onto a $C_{18}$ reverse phase liquid chromatography column (Vydac, Hesperia, Calif.) with a Perkin Elmer ISS 100 autosampler and eluted with a gradient of 0–50% $CH_3CN$ in 0.1% $CF_3CO_2H$ at 2 ml/min. Peptide product peaks were monitored at 220 nm with a Perkin Elmer LC 95 detector and integrated with Rainin Dynamax software in order to quantitate activity.

Assay 2

CATHEPSIN D INHIBITION ACTIVITY (NON-CELLULAR FLUOROMETIC ASSAY)

A fluorometric assay was adapted from the method disclosed by Murakami et al., (1981) Anal. Biochem. 110:232–239 for measuring renin activity. Human liver cathepsin D (Athens Research and Technology, Athens, Ga.) was diluted in assay buffer, 200 mM NaOAc, pH 4.5, 150 mM NaCl to 500 ng/ml and then 100 µL of this cathepsin D solution was added to each well of a 96 well plate with the exception of control wells which received just 100 µL of assay buffer. Compound stocks were prepared by dissolving an aspartyl protease inhibitor in DMSO for each concentration tested in the assay and then 5 µL of compound stock was added to each of the wells prepared above. Blank and enzyme control wells each received 5 µL of the DMSO vehicle.

Following a ten minute incubation at 25° C. to allow enzyme/compound interaction, 5 µl of 500 µM fluorometric substrate (Bachem Biosciences, Philadelphia, Pa.) in dimethylsulfoxide was added per well to initiate the reaction. After incubation at 37° C. for 30 minutes, cathepsin D activity was terminated by the addition of 100 µL per well of 400 mU/ml microsomal leucine aminopeptidase (EC 3.4.11.2, Sigma, St. Louis, Mo.) in 1M Tris-HCl, pH 8.0.

The plates were then analyzed in a fluorometer (CytoFluor 2350, Millipore, Bedford, Mass.) with an excitation wavelength of 360 nm and an emission wavelength of 460 nm, in order to check for background fluorescence due to test compounds. Following a two hour incubation at 37° C., to allow the aminopeptidase to release the fluorophore, 7-amido-4-methylcoumarin (AMC) from the products of cathepsin D cleavage, the plates were again analyzed in the fluorometer. In order to check for potential false positives, i.e., inhibitors of microsomal leucine aminopeptidase, residual aminopeptidase activity was monitored directly in each well by the addition of 20 µL/well of 2.5 mM Leu-pNA (Bachem Biosciences, Philadelphia, Pa.) in 10% DMSO. Aminopeptidase activity was measured as an increase in the absorbance at 405 nm in a $UV_{max}$ microplate reader (Molecular Devices, Menlo Park, Calif.).

Cathepsin D activity was linear under these conditions and the results are expressed as a percentage of the controls in Tables 4 and 5, below. All results presented are the mean and standard deviation of at least four replicate assays.

Assay 3

CATHEPSIN D INHIBITION ACTIVITY (NON-CELLULAR ASSAY)

A third non-cellular assay for determining in vitro aspartyl protease inhibitory activity is generally described in Jupp, R. A. et al., (1990) Biochem. J., 265:871–878 and Rao et al., J. Med. Chem. (1993), in press. The assay is carried out by incubating a test compound with a suitable aspartyl protease, such as cathepsin D, in the presence of a chromogenic substrate. The inhibition constant, $K_i$, value may then be determined by quantifying the competitive inhibition of the hydrolysis of the chromogenic substrate. A variety of chromogenic substrates that are useful for assaying aspartyl protease activity are discussed in Dunn, et al., (1986) Biochem. J., 237:899–906. A preferred chromogenic substrate for a cathepsin D assay is disclosed in Scarborough, P. E. et al., Protein Science, (1993), 2:264–276.

Concentrations of substrate solutions and cleavage products may be verified using amino acid analysis. The enzyme preparations may be titrated with a tightly binding inhibitor to quantitate the active concentration of the enzyme. Enzyme concentrations are typically in the range of from 1–6 nM. Stock solutions of the test compound are prepared at concentrations ranging from 1.0 to 5.0 mg/ml, and then 50–100 µl portions of these stock solutions may be further diluted to a concentration in the range of 5 to 300 µM for rate determinations.

First, the percentage of inhibition of the initial rate of reaction in the presence of 4 mM of the test compound may be determined relative to a control reaction in order to provide an estimate of the test compound's potency. Then, the test compounds are assayed over a concentration range of, for example, 5 to 300 µM for rate determinations.

A decrease in absorbance in the range of 284–324 nm may be monitored using a spectrophotometer. Absorbance readings are typically taken at various timepoints. The initial velocities are then plotted versus the initial substrate concentration. The kinetic parameter, $K_m$ for the chromogenic substrate may be calculated from these data. Estimates of $K_i$ may then be determined using the Dixon construction. Dixon, M., (1953) Biochem J., 55:170–171.

If the ratio of the total active enzyme concentration to the estimated $K_i$ value ($[E]/K_i$) is less than 0.2, then the precise $K_i$ value may be computed by using a non-linear curve fitting program based on the equation:

$$v = V_{max}[S]/[S] + K_m(1+[I]/K_i)$$

where v is the initial rate, [S] is the initial substrate concentration, [I] is the inhibitor concentration and $K_m$ and $K_i$ are defined above. If the ratio, $[E]/K_i$, is between 0.2 and 10, then the precise $K_i$ value may be calculated using the method described in Henderson, P. J. F., (1972) Biochem J., 127:321–333. This Assay is exemplified in Assay 3.

CATHEPSIN D INHIBITION ACTIVITY (NON-CELLULAR ASSAY)

An assay for measuring aspartyl protease activity using a chromogenic substrate was used to determine the inhibition constant, $K_i$, for the test compounds Frozen human placental tissue was thawed and homogenized in 10 mM Tris-HCl, pH 7.4, and 0.5% Brij 35 in a Waring blender. The homogenate was centrifuged at 10,000 rpm for 30 minutes in a Sorvall GSA rotor. The supernatant was adjusted to pH 3.7 using 5.7N HCl and then sodium acetate was added to a concentration of 0.1M. The resultant mixture was incubated for 30 minutes at 0° C., resulting in the formation of a precipitate. This precipitate was removed by centrifugation (30 minutes, 10,000 rpm). The acidic supernatent was applied to a chromatography column (pepstatinyl agarose equilibrated with 0.1M sodium acetate, pH 3.5, 0.1% Brij 35, and 1M NaCl), washed until the OD$_{280}$ of the effluent returned to baseline, and then eluted with 50 mM Tris-HCl, pH 8.6, 0.1% Brij 35, and 1M NaCl. The eluent was dialyzed against 10 mM sodium phosphate, pH 7.0, 0.1% Brij 35, and 0.1M NaCl, and then applied to a 1 ml DEAE-Sephacel column equilibrated with the same buffer. Cathepsin D was recovered in the breakthrough fraction.

The enzyme mixture (125 µl buffer (0.1M sodium formate at pH 3.7), 1 µL of a 1 mm solution of test compound, 4 µL of DMSO, enzyme and water to provide a total volume of 230 µL) was vortexed and prewarmed for four minutes before the addition of the chromogenic substrate. After warming, the enzyme mixture was added to 20 µL of a 625 µL dilution of substrate solution. A control reaction mixture was similarly prepared without the addition of the the test compound. The percent of inhibition of the initial rate of reaction in the presence of a particular concentration of test compound (i.e. 4 µM) may be determined for the test compound by monitoring the reaction mixture in parallel to the control reaction.

The decrease in absorbance in the range of 284–324 nm was followed on a Hewlett-Packard 8452A diode array spectrophotometer equipped with a multi-cell transport and thermostatted at 37° C. Absorbance readings were taken at 0.1 second intervals every 2 nm over the targeted range. Each cuvette was sampled five times; the resultant readings were averaged for each time point. For each cuvette, the reading was repeated with a cycle time of 17.2 seconds for approximately 1000 seconds.

The initial velocity was calculated from the slope during the linear phase of the reaction and then plotted versus substrate concentration at the start of the reaction. These data were fitted to the standard Michaelis-Menten equation by Marquardt analysis to yield the calculated value, $K_m$, for the substrate. The values of $K_i$ were estimated using the Dixon construction, and then calculated using a nonlinear curve-fitting program ($[E]/K_i<0.2$) or the Henderson method ($0.2<[E]/K_i<10$) as described above.

TABLE 1

| Cathepsin D Inhibition Assay | | |
|---|---|---|
| Example Number | Concentration (µg/ml) | Percent Inhibition |
| 1 | 10.0 | 60 |
|  | 0.31 | 4 |
|  | 0.62 | 0 |
|  | 1.25 | 15 |
|  | 2.50 | 15 |
|  | 5.00 | 26 |
|  | 10.0 | 45 |
| 19 | 10.0 | 67 |
|  | 0.31 | 14 |
|  | 0.62 | 19 |
|  | 1.25 | 15 |
|  | 2.50 | 24 |
|  | 5.00 | 41 |
|  | 10.0 | 69 |
|  | 1.25 | 21 |
|  | 2.50 | 33 |
|  | 5.00 | 51 |
|  | 10.0 | 74 |
| 2 | 10.0 | 38 |
| 3 | 10.0 | 14 |
| 4 |  |  |
| 5 | 10.0 | 28 |
| 6 | 10.0 | 46 |
| 7 | 10.0 | 41 |
| 16 | 10.0 | 20 |
| 21 | 10.0 | 25 |
| 8 | 10.0 | 0 |
| 9 | 10.0 | 14 |

Upon identification of aspartyl protease inhibitors, further screening was performed to select those aspartyl protease inhibitors which inhibit the intracellular production of β-amyloid peptide. The β-amyloid peptide production inhibition activity is typically measured in a cellular assay or in an animal model, or both.

The cellular assay preferably utilizes a cell line which has been transfected to overproduce β-amyloid peptide, such as a cell line which has been transfected with the Swedish or other mutation responsible for AD or other β-amyloid peptide-related condition. Typically these assays measure β-amyloid peptide production in a test system in which the aspartyl protease inhibitor has been administered and in a control test system in which no such aspartyl protease inhibitor has been administered in order to measure a reduction in β-amyloid peptide production relative to the control. These assays may measure β-amyloid peptide production or the presence of a cellular characteristic which is related to β-amyloid peptide production. Aspartyl protease inhibitors which inhibit or otherwise affect intracellular β-amyloid peptide production will typically be tested further.

The test system used to measure the β-amyloid peptide production inhibition activity is typically a cellular assay or an animal model. Preferably, the β-amyloid peptide production inhibition activity is obtained by direct measurement of β-amyloid peptide production in a cellular assay, as described in copending United States patent application Ser. No. 07/965,972, the full disclosure of which is incorporated herein by reference. This assay is exemplified in Assay 4, below.

For example, mammalian cell lines, typically human cell lines, are grown under conditions which result in the secretion of detectable amounts of β-amyloid peptide into the conditioned culture media, typically in the range of from about 0.1 ng/ml to 10 ng/ml. By growing cells under conditions which result in the accumulation of β-amyloid peptide in the conditioned culture medium, and exposing the cultured cells to an aspartyl protease inhibitor, it is possible to measure the effect of the aspartyl protease inhibitor on β-amyloid peptide production. An aspartyl protease inhibitor which diminishes β-amyloid peptide production is useful for the therapeutic treatment of Alzheimer's Disease and other β-amyloid peptide-related conditions.

Typical cell lines used in the cellular assay include human and animal cell lines, such as the 293 human kidney cell line, human neuroglioma cell lines, human HeLa cells, primary human endothelial cells (e.g., HUVEC cells), primary human fibroblasts or lymphoblasts, primary human mixed brain cells, including neurons, astrocytes, and neuroglia, Chinese hampster ovary (CHO) cells, and the like. Preferred are cell lines capable of expressing amyloid precursor protein variants which overproduce β-amyloid peptide. As used herein, the term "overproduce" means that the amount of β-amyloid peptide produced from the variant amyloid precursor protein will be greater than the amount produced from any or all of the normal amyloid precursor protein isoforms. Particularly preferred amyloid precursor protein variants are those having one or several amino acid substitutions directly adjacent (toward the amino-terminus) to the β-amyloid peptide cleavage site. For example, K293 cells which express an amyloid precursor protein containing the Swedish mutation produce approximately six-fold to eight-fold more β-amyloid peptide than cells expressing normal amyloid precursor protein.

β-amyloid peptide may be measured in the conditioned culture medium by any technique which is sufficiently selective and sensitive to identify substantially intact β-amyloid peptide in the presence of other amyloid precursor protein fragments which may be present. Immunological detection techniques may be employed using binding substances specific for β-amyloid peptide, such as antibodies, antibody fragments, recombinant antibodies, and the like, which possess the requisite specificity and sensitivity to β-amyloid peptide. Antibodies which are monospecific for the junction region of β-amyloid peptide are capable of distinguishing β-amyloid peptide from other fragments. As used herein the term "β-amyloid peptide junction region" refers to that region of β-amyloid peptide which is centered at the site between amino acid residues 16 and 17 ($Lys_{16}$ and $Leu_{17}$) The β-amyloid peptide junction region is a target for normal proteolytic processing of amyloid precursor protein. Such normal processing results in a variety of amyloid precursor protein fragments which are potentially immunologically cross-reactive with the intact β-amyloid peptide molecule. Antibodies raised against a synthetic peptide consisting of amino acid residues 13–28 of β-amyloid peptide have been found to display the requisite specificity.

Suitable detection techniques include ELISA, Western blotting, radioimmunoassay, and the like. A typical cellular assay for assaying β-amyloid peptide production is described in copending application Ser. No. 07/965,971, the full disclosure of which is incorporated herein by reference. This assay relies on the measurement of a fragment of amyloid precursor protein (other than the β-amyloid peptide fragment) which is produced and secreted into the cell culture as a result of β-amyloid peptide production. The secreted fragments comprise a substantially intact amino-terminal sequence of amyloid precursor protein terminating within five amino acids of the carboxy-terminal residue (methionine in the case of the normal amyloid precursor protein sequence) which lies adjacent to the β-amyloid peptide region and intact amyloid precursor protein. In particular, the secreted fragments may consist essentially of sequences which terminate in $Met_{596}$ and $Lys_{595}$ of the 695 amino acid isoform of amyloid precursor protein, with corresponding numbering for the other isoforms and corresponding amino acids for the mutant amyloid precursor protein forms, such as $Lys_{595}$-$Met_{596}$ to $Asn_{595}$-$Leu_{596}$ for the Swedish mutation.

A preferred detection technique includes a two-site or "sandwich" assay employing a junction-specific antibody as the capture antibody which is bound to a solid phase and a second labelled antibody which binds to an epitope other than that bound by the capture antibody. The second labelled antibody preferably recognizes the amino-terminus of β-amyloid peptide and may be conveniently raised against a synthetic peptide consisting essentially of amino acid residues 1–16 of β-amyloid peptide.

Alternatively, β-amyloid peptide production may be monitored in an animal model, such as the mouse animal model disclosed in WO 91/19810. An animal model that expresses another amyloid precursor protein isotype and/or variant may also be used to screen aspartyl protease inhibitors. Testing in an animal model will typically be performed in addition to the cellular assay described supra. The β-amyloid peptide production in a body fluid of a test animal may be measured by assaying for the presence of β-amyloid peptide or a β-amyloid peptide fragment in a body fluid of the test animal before and after the administering of an aspartyl protease inhibitor.

The present invention provides methods for inhibiting β-amyloid peptide production in cells, comprising administering to the cells an aspartyl protease inhibitor selected by the process described above. For example, the aspartyl protease inhibitor may be added to a cell culture in order to inhibit β-amyloid peptide production by the cultured cells. Alternatively, the aspartyl protease inhibitor may be administered to a mammal in need thereof in order to inhibit the production of β-amyloid peptide and subsequently the deposition of armyloid plaque associated with Alzheimer's Disease and other β-amyloid peptide-related diseases.

The following assays are offered by way of illustration, not by way of limitation. These assays were carried out to demonstrate the ability of the compounds used in the methods of the present invention to inhibit aspartyl proteases, particularly cathepsin D.

Assay 4

β-AMYLOID PEPTIDE PRODUCTION INHIBITION (CELLULAR ASSAY)

Two cell lines (human kidney cell line 293 and Chinese hamster ovary cell line CHO) were stably transfected with the gene for APP751 containing the double mutation $Lys_{651}$-$Met_{652}$ to $Asn_{651}$-$Leu_{652}$ (APP-751 numbering) commonly called the Swedish mutation using the method described in Citron, et al., Nature 360:672-674 (1992). The transfected cell lines were designated as 293 751 SWE and CHO 751 SWE, and were plated in Corning 96 well plates at $2.5 \times 10^4$ or $1 \times 10^4$ cells per well respectively in Dulbecco's minimal essential media (DMEM) plus 10% fetal bovine serum. Following overnight incubation at 37° C. in an incubator equilibrated with 10% carbon dioxide ($CO_2$), the media were removed and replaced with 200 μl per well of media containing an aspartyl protease inhibitor. After a two hour pretreatment period, the media were again removed and replaced with fresh media containing the aspartyl protease inhibitor and the cells were incubated for an additional two hours.

Aspartyl protease inhibitor stocks were prepared in DMSO such that at the final concentration used in the treatment, the concentration of DMSO did not exceed 0.5%. After treatment, plates were centrifuged at 1200 rpm for five minutes at room temperature to pellet cellular debris from the conditioned media. From each well, 100 μl of conditioned media were transferred into an ELISA plate precoated with antibody 266 against β-amyloid peptide(13-28) (Seubert et al., supra. ) and stored at 4° C. overnight. An ELISA assay employing labelled antibody 6C6 (against β-amyloid peptide-1-16) was run the next day to measure the amount of β-amyloid peptide produced.

Cytotoxic effects of the compounds were measured by a modification of the method of Hansen et al., (1989) J. Immun. Meth. 119:203-210. To the cells remaining in the tissue culture plate, was added 25 μl of a 3-(4,5-dimethylthiazol-2-yl)2,5-diphenyltetrazolium bromide (MTT) stock solution (5 mg/ml) to a final concentration of 1 mg/ml. Cells were incubated at 37° C. for one hour, and cellular activity was stopped by the addition of an equal volume of MTT lysis buffer (20% w/v sodium dodecylsulfate in 50% DMF, pH 4.7). Complete extraction was achieved by overnight shaking at room temperature. The difference in the $OD_{562nm}$ and the $OD_{650nm}$ was measured in a $Uv_{max}$ microplate reader as an indicator of the cellular viability.

The results of the β-amyloid peptide ELISA were fit to a standard curve and expressed as ng/ml β-amyloid peptide. In order to normalize for cytotoxicity, these β-amyloid peptide results were divided by the MTT results and expressed as a percentage of the results from a drug-free control.

TABLE 8

β-Amyloid Peptide Production Inhibition Activity In Cells

| Example Number | Concentration (μg/ml) | Percent Inhibition |
|---|---|---|
| 1 | 10.0 | 60 |
|   | 0.31 | 4 |
|   | 0.62 | 0 |
|   | 1.25 | 15 |
|   | 2.50 | 15 |
|   | 5.00 | 26 |
|   | 10.0 | 45 |
| 3 | 10.0 | 67 |
|   | 0.31 | 14 |
|   | 0.62 | 19 |
|   | 1.25 | 15 |
|   | 2.50 | 24 |
|   | 5.00 | 41 |
|   | 10.0 | 69 |
|   | 1.25 | 21 |
|   | 2.50 | 33 |
|   | 5.00 | 51 |
|   | 10.0 | 74 |
| 4 | 10.0 | 38 |
| 5 | 10.0 | 14 |
| 7 | 10.0 | 28 |
| 8 | 10.0 | 46 |
| 10 | 10.0 | 41 |
| 11 | 10.0 | 20 |
| 13 | 10.0 | 25 |
| 14 | 10.0 | 0 |
| 15 | 10.0 | 14 |

The compounds of Formula I are usually administered in the form of pharmaceutical compositions. These compounds can be administered by a variety of routes including oral, rectal, transdermal, subcutaneous, intravenous, intramuscular, and intranasal. Such compositions are prepared in a manner well known in the pharmaceutical art and comprise at least one active compound.

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 225 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycer-

43

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| 4Active Ingredient | 15.0mg |
| Starch | 407.0mg |
| Magnesium stearate | 3.0mg |
| Total | 425.0mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
| --- | --- |
| Active Ingredient | 250.0 mg |
| N-Methylglucamine | 375.0 mg |
| Isotonic saline | 1000 ml |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The active ingredient is added and stirring is continued until dispersed. The mixture is then cooled until solid.

Other preferred formulations employed in the methods of the present invention utilize transdermal delivery devices ("patches"). Such transdermal patches may be used to provide continuous or discontinuous infusion of the compounds of the present invention in controlled amounts. The construction and use of transdermal patches for the delivery of pharmaceutical agents are well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

The compounds of the present invention can be administered for prophylactic and/or therapeutic treatment of diseases related to the deposition of β-amyloid peptide, such as Alzheimer's disease, Down's syndrome, and advanced aging of the brain. In therapeutic applications, the compounds are administered to a host already suffering from the disease. The compounds will be administered in an amount sufficient to inhibit further deposition of β-amyloid plaque. The specific dose of compound administered according to this invention to obtain therapeutic and/or prophylactic effects will, of course, be determined by the particular circumstances surrounding the case, including, for example, the compound administered, the route of administration, the condition being treated, the individual being treated and the like. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

For prophylactic applications, the compounds of the present invention are administered to a host susceptible to Alzheimer's Disease or a β-amyloid peptide-related disease, but not already suffering from such disease. Such hosts may be identified by genetic screening and clinical analysis, as described in the medical literature. See e.g., L. Goate, *Nature (London)*, 349:704–706 (1991). The compounds will be able to inhibit or prevent the formation of β-amyloid plaque at a symptomatically early stage, preferably preventing even the initial stages of the β-amyloid-associated disease.

We claim:

1. A compound of the formula $$R-(CH_2)_n-A-(CH_2)_q- \text{[structure]} -N-R^1$$

wherein:

n is 0, 1, 2, 3, or 4;

q is 0, 1, 2, 3, or 4;

A is —O—, —NH—, or —S(O)$_m$—;

where m is 0, 1, or 2;

R$^1$ is hydrogen, C$_1$–C$_6$ alkyl, di(C$_1$–C$_6$ alkyl)amino-, amino, (C$_1$–C$_6$ alkyl)amino-, cyano(C$_1$–C$_6$ alkyl)-, or carboxy(C$_1$–C$_6$ alkylidene)-;

R is phenyl, oxazolyl, benzophenonyl, or naphthyl optionally substituted with one or more substituents selected from the group consisting of C$_1$–C$_{10}$ alkyl, C$_2$–C$_{10}$ alkanoyl, hydroxy, nitro, rhodanine, C$_2$–C$_{10}$ alkanoyloxy, hydrogen, phenyl, phenyl($C_1$–$C_6$ alkylidenyl)-, heterocycle, heterocycle($C_1$–$C_6$ alkylidenyl)-, unsaturated heterocycle, unsaturated heterocycle($C_1$–$C_6$ alkylidenyl)-, halo, $C_1$–$C_{10}$ alkylamino, $C_1$–$C_{10}$ alkoxy, benzoyl, and $C_1$–$C_{10}$ alkylthio, said phenyl, phenyl($C_1$–$C_6$ alkylidenyl)-, benzoyl, heterocycle, heterocycle($C_1$–$C_6$ alkylidenyl)-, unsaturated heterocycle($C_1$–$C_6$ alkylidenyl)-, rhodanine, and unsaturated heterocycle moieties being optionally substituted with one or more halo, $C_1$–$C_6$ alkyl, hydroxy, carboxy, or $C_1$–$C_6$ alkoxy groups;

with the proviso that if q is 0, $R^1$ is hydrogen, and n is 0 or 2, then R is not unsubstituted phenyl;

or a pharmaceutically acceptable salt thereof.

2. A compound as claimed in claim 1 wherein A is —O—.

3. A compound as claimed in claim 2 wherein R is substituted phenyl.

4. A compound as claimed in claim 3 wherein at least one substitution of the phenyl group is at the two position.

5. A compound as claimed in claim 4 wherein the substitution at the two position of the phenyl group is $C_1$–$C_6$ alkyl.

6. A compound as claimed in claim 5 wherein the substitution at the two position of the phenyl group is propyl.

7. A compound as claimed in claim 6 wherein the phenyl group is further substituted at the four position.

8. A compound as claimed in claim 1 wherein n is 0, 1, or 2.

9. A pharmaceutical formulation comprising an effective amount of a compound of the formula

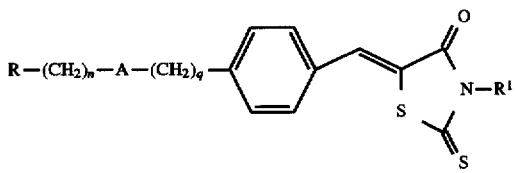

wherein:
n is 0, 1, 2, 3, or 4;
q is 0, 1, 2, 3, or 4;
A is —O—, —NH—, or —S(O)$_m$—;
where m is 0, 1, or 2;
$R^1$ is hydrogen, $C_1$–$C_6$ alkyl, di($C_1$–$C_6$ alkyl)amino-, amino, ($C_1$–$C_6$ alkyl)amino-, cyano($C_1$–$C_6$ alkyl)-, or carboxy($C_1$–$C_6$ alkylidene)-;

R is phenyl, oxazolyl, benzophenonyl, or naphthyl optionally substituted with one or more substituents selected from the group consisting of $C_1$–$C_{10}$ alkyl, $C_2$–$C_{10}$ alkanoyl, hydroxy, nitro, rhodanine, $C_2$–$C_{10}$ alkanoyloxy, hydrogen, phenyl, phenyl($C_1$–$C_6$ alkylidenyl)-, heterocycle, heterocycle($C_1$–$C_6$ alkylidenyl)-, unsaturated heterocycle, unsaturated heterocycle($C_1$–$C_6$ alkylidenyl)-, halo, $C_1$–$C_{10}$ alkylamino, $C_1$–$C_{10}$ alkoxy, benzoyl, and $C_1$–$C_{10}$ alkylthio, said phenyl, phenyl($C_1$–$C_6$ alkylidenyl)-, benzoyl, heterocycle, heterocycle($C_1$–$C_6$ alkylidenyl)-, unsaturated heterocycle($C_1$–$C_6$ alkylidenyl)-, rhodanine, and unsaturated heterocycle moieties being optionally substituted with one or more halo, $C_1$–$C_6$ alkyl, hydroxy, carboxy, or $C_1$–$C_6$ alkoxy groups;

with the proviso that if q is 0, $R^1$ is hydrogen, and n is 0 or 2, then R is not unsubstituted phenyl;

or a pharmaceutically acceptable salt thereof, in combination with one or more pharmaceutically acceptable carriers, diluents, or excipients therefor.

10. A formulation as claimed in claim 9 employing a compound wherein A is —O—.

11. A formulation as claimed in claim 10 employing a compound wherein R is substituted phenyl.

12. A formulation as claimed in claim 11 employing a compound wherein at least one substitution of the phenyl group is at the two position.

13. A formulation as claimed in claim 12 employing a compound wherein the substitution at the two position of the phenyl group is $C_1$–$C_6$ alkyl.

14. A formulation as claimed in claim 13 employing a compound wherein the substitution at the two position of the phenyl group is propyl.

15. A formulation as claimed in claim 14 employing a compound wherein the phenyl group is further substituted at the four position.

16. A formulation as claimed in claim 9 employing a compound wherein n is 0, 1, or 2.

* * * * *

UNITED STATES PATENT AND TRADEMARK OFFICE
CERTIFICATE OF CORRECTION

PATENT : 5,747,517

DATED : May 5, 1998

INVENTOR(S) : Jill A. Panetta, et al

It is certified that error appears in the above-identified patent and that said Letters Patent is hereby corrected as shown below:

Column 7, line 45, reads "OC" and should read --0°C--.

Column 15, line 8, reads "$H_23$" and should read --$H_{23}$--.

Column 15, line 36, reads "$H_23$" and should read --$H_{23}$--.

Column 16, line 29, reads "NO2S" and should read --$NO_2S$--.

Column 18, line 19, reads "103°" and should read --108°--.

Column 25, line 37, reads "OC" and should read --0°C--.

Column 25, line 41, reads "OC" and should read --0°C--.

Column 39, line 1, reads "armyloid" and should read --amyloid--.

Signed and Sealed this

Ninth Day of May, 2000

*Attest:*

Q. TODD DICKINSON

*Attesting Officer*  *Director of Patents and Trademarks*